US008683672B2

(12) United States Patent
Deshusses et al.

(10) Patent No.: US 8,683,672 B2
(45) Date of Patent: Apr. 1, 2014

(54) NANOMATERIAL-BASED GAS SENSORS

(71) Applicant: The Regents of the University of California, Oakland, CA (US)

(72) Inventors: Marc A. Deshusses, Riverside, CA (US); Nosang V. Myung, Riverside, CA (US); Wayne Bosze, Las Vegas, NV (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/672,632

(22) Filed: Nov. 8, 2012

(65) Prior Publication Data

US 2013/0062211 A1  Mar. 14, 2013

Related U.S. Application Data

(62) Division of application No. 12/514,050, filed as application No. PCT/US2007/084350 on Nov. 9, 2007, now abandoned.

(60) Provisional application No. 60/910,434, filed on Apr. 5, 2007, provisional application No. 60/965,218, filed on Nov. 10, 2006.

(51) Int. Cl.
*G01N 15/06* (2006.01)
*G01N 15/00* (2006.01)

(52) U.S. Cl.
USPC ............... 29/592.1; 422/50; 422/83; 422/96; 977/924; 29/592

(58) Field of Classification Search
USPC ......... 422/50, 83, 98; 977/924; 29/592, 592.1
See application file for complete search history.

(56) References Cited

U.S. PATENT DOCUMENTS

| 6,586,095 B2 | 7/2003 | Wang et al. |
| 7,122,106 B2 | 10/2006 | Lin et al. |
| 2002/0179434 A1 | 12/2002 | Dai et al. |
| 2003/0217928 A1* | 11/2003 | Lin et al. ............... 205/109 |

(Continued)

FOREIGN PATENT DOCUMENTS

| WO | WO02/37536 | 5/2002 |
| WO | WO2004/083282 | 9/2004 |

OTHER PUBLICATIONS

Kong et al.; "Functionalized Carbon Nanotubes for Molecular Hydrogen Sensors"; Advanced Materials; pp. 1384-1386; Sep. 14, 2001, 13, No. 18.

(Continued)

*Primary Examiner* — Brian J Sines
(74) *Attorney, Agent, or Firm* — Klein, O'Neill & Singh, LLP

(57) ABSTRACT

A gas sensing device (nanosensor) includes a substrate with at least a pair of conductive electrodes spaced apart by a gap, and an electrochemically functionalized semiconductive nanomaterial bridging the gap between the electrodes to form a nanostructure network. The nanomaterial may be single-walled carbon nanotubes (SWNTs) functionalized by the deposition of nanoparticles selected from the group consisting of an elemental metal (e.g., gold or palladium), a doped polymer (e.g., camphor-sulfonic acid doped polyaniline), and a metal oxide (e.g. tin oxide). Depending on the nanoparticles employed in the functionalization, the nanosensor may be used to detect a selected gas, such as hydrogen, mercury vapor, hydrogen sulfide, nitrogen dioxide, methane, water vapor, and/or ammonia, in a gaseous environment.

15 Claims, 20 Drawing Sheets

(56) References Cited

U.S. PATENT DOCUMENTS

| | | | |
|---|---|---|---|
| 2005/0045477 A1 | 3/2005 | Wei et al. | |
| 2005/0157445 A1 | 7/2005 | Bradley et al. | |
| 2005/0165155 A1 | 7/2005 | Blanchet-Fincher | |
| 2006/0246438 A1 | 11/2006 | McCall et al. | |
| 2009/0266411 A1* | 10/2009 | Habib et al. | 136/255 |
| 2010/0203648 A1* | 8/2010 | Porter et al. | 436/109 |

OTHER PUBLICATIONS

Kong et al.; "Nanotube Molecular Wires as Chemical Sensors"; Science; vol. 287, pp. 622-625; Jan. 28, 2000; www.sciencemag.org.

Trafton; "MIT's 'electronic nose' could detect hazards"; MIT Tech Talk; p. 4; Oct. 31, 2007.

Zhang; "Electrochemically Functionalized Single-Walled Carbon Nanotube Gas Sensor"; Electroanalysis, 2006; vol. 18, No. 12, pp. 1153-1158; Feb. 28, 2006.

International Search Report on corresponding PCT application (PCT/US2007/084350) from International Searching Authority (USPTO) dated Oct. 15, 2008.

Written Opinion on corresponding PCT application (PCT/US2007/084350) from International Searching Authority (USPTO) dated Oct. 15, 2008.

\* cited by examiner

Sensor response to methane for different concentrations

Sensor response to ammonia for different concentrations

NANOMATERIAL-BASED GAS SENSORS

CROSS-REFERENCE TO RELATED APPLICATIONS

This application is a divisional of application Ser. No. 12/514,050 filed Dec. 22, 2009, which is a national phase filing, under 35 U.S.C. §371(c), of International Application No. PCT/US2007/084350, filed Nov. 9, 2007, which claims the benefit, under 35U.S.C. §119(e), of U.S. provisional application Ser. No. 60/910,434, filed Apr. 5, 2007, and U.S. provisional application Ser. No. 60/865,218, filed Nov. 10, 2006, the disclosures of which are incorporated herein by reference in their entireties.

FEDERALLY SPONSORED RESEARCH OR DEVELOPMENT

Not Applicable

BACKGROUND OF THE INVENTION

1. Field of the Invention

The present invention relates to gas sensors, and more particularly, to electrochemically functionalized, nanomaterial-based gas sensors.

2. Description of Related Art

Gas detection instruments or gas sensors have a wide range of applications, including industrial health and safety, environmental monitoring, and process control. Some of the fields in which gas sensors are used include chemical refining, petroleum refining, rocket fuel production, fuel cell manufacturing, semiconductor processing, and biomedical applications. In one example of a biomedical application, hydrogen gas sensors may be used to detect hydrogen in exhaled breath. The presence and concentration of exhaled hydrogen may be used to diagnose various diseases, including lactose intolerance, fructose malabsorption, fibromyalgia and neonatal necrotizing enterocolitis.

Typically, gas sensor reactions occur at elevated temperatures. Therefore, the operating temperatures of both the sensor material and the gas to be detected must be controlled for optimal response, which typically means that the sensors must be heated. In addition, the sensors should have a large ratio of surface area to volume to increase the opportunities for surface reactions. Gas sensors made of nanoscale materials exhibit the desirable large ratio of surface area to volume. For example, single-walled carbon nanotubes (SWNTs) are considered ideal building blocks for making gas sensors, as all the carbon atoms in SWNTs are exposed to the surface, providing abundant surface area per unit volume.

Nanoscale materials (also referred to as "nanomaterials") are defined as having at least one physical dimension in the range of 1-100 nanometers. These materials, such as carbon nanotubes, can be either semiconductive or conductive, depending on their diameter and helicity. Semiconductive and conductive nanomaterials can exhibit sensitivity to gases. For example, carbon SWNTs are particularly advantageous for making gas sensors, because all of their carbon atoms are exposed to the outer surface of the structure, thereby providing more surface area exposed to the gas. With their unique electrical, thermal, and mechanical properties, SWNTs exhibit better sensitivity compared to conventional bulk materials in a transistor configuration for the detection of gases such as hydrogen ($H_2$), hydrogen sulfide ($H_2S$), ammonia ($NH_3$), nitrogen dioxide ($NO_2$), water vapor, and methane. Other nanomaterials with semiconductive properties have shown promise for use as gas sensors.

The sensing mechanism of a semiconductive nanomaterial-based gas sensor depends upon charge transfer between the electron-donating/electron-withdrawing molecules of the gas and the semiconducting nanostructures. Such electron donation or withdrawal changes the conductivity of the nanomaterial. Nanomaterial-based sensors, therefore, using low-power microelectronics technology, convert chemical information into an electrical signal, leading to the formation of miniaturized sensor devices.

However, bare nanomaterial-based sensors do not exhibit high sensitivity toward certain gases due to their low absorption capacity. This less-than-ideal sensitivity, as well as relatively low selectivity, has limited the use of nanomaterial-based gas sensors in practical applications.

Current methods for using some nanomaterial-based gas sensors require highly reactive reagents and high temperatures to modify the nanomaterial structure and to make the materials suitable to act as gas sensors. In addition, functionalization of the sensors requires long fabrication time and complicated fabrication steps, which makes the process complex and costly. These functionalization techniques also have limited spatial resolution, which makes the creation of high density sensor arrays difficult.

Carbon nanotubes (CNTs) and one dimensional nanostructures such as nanowires have been demonstrated as appealing sensing materials for developing advanced chemical gas sensors. Based on the mechanism of charge transfer, gas adsorption (e.g., $NO_2$, $NH_3$, $O_2$) can cause significant electrical transport property changes in the CNTs and nanowires. Compared to traditional thin film or thick film sensing materials. CNTs and nanowires offer several advantages, such as good sensitivity, room temperature operation, and fast response time due to their quasi one-dimensional structure, large surface area-to-volume ratio, small size, and unique electrical properties. However, the number of analytes that can be detected by pristine CNTs is limited to only a few types, such as CO and hydrogen.

Relative humidity (RH) is one major environmental factor that affects performance of most chemical gas sensors, including CNT sensors. For example, experimental measurements have demonstrated that some SWNTs and some multi-walled carbon nanotubes (MWNTs) exhibit increased resistance when interacted with atmospheric moisture (water vapor) in non-condensing conditions. One explanation for this increased resistance is that electron-donating water molecules deplete the hole charge carriers of p-type CNTs, thereby increasing the resistivity of the CNTs. Thus, minimizing or eliminating the RH effect is desirable for the reliable application of CNT gas sensors.

SUMMARY OF THE DISCLOSURE

The preferred embodiments of the presently-disclosed nanomaterial-based gas sensors and methods for producing nanomaterial-based gas sensors have several features, no single one of which is solely responsible for their desirable attributes. Without limiting the scope of these gas sensors and methods as defined by the claims that follow, their more prominent features will now be discussed briefly. After considering this discussion, and particularly after reading the section of this specification entitled "Detailed Description of the Preferred Embodiments," one will understand how the features of the various embodiments disclosed herein provide a number of advantages over the current state of the art. These advantages include, without limitation, simplified and more efficient methods of fabricating functionalized nanomaterial-based gas sensors having outstanding sensing properties, including high sensitivity, low detection limits, fast response and recovery times, good reproducibility, good selectivity in the detection of gases, and long term stability within a wide temperature range.

Another advantage of the presently-disclosed gas sensors is the elimination of the relative humidity effect on CNT sensors and functionalized CNT sensors, thereby eliminating (or at least minimizing) the need to compensate for the RH effect under varying RH conditions.

Broadly, this disclosure, in one aspect, relates to a gas sensing device comprising a substrate layer having at least a pair of conductive (e.g., metallic) electrodes formed thereon, the electrodes defining a gap between them. An electrochemically functionalized nanomaterial bridges the gap between the electrodes to form a nanostructure network. The nanomaterial is functionalized by a surface deposition or coating of a functionalization material selected from the group consisting of metallic nanoparticles, doped polyaniline nanoparticles, and metal oxide nanoparticles.

In another aspect, this disclosure relates to a method for forming a gas sensing device, wherein the method comprises (a) forming a nanostructure network, and (b) functionalizing the nanostructure network The functionalization is performed by electrodepositing on the nanostructure network a surface distribution of nanoparticles selected from the group consisting of metallic nanoparticles, doped polyaniline nanoparticles, and metal oxide nanoparticles.

More specifically, one embodiment of the presently disclosed method for forming a nanostructure network comprises (a) microfabricating an array of electrodes on a substrate, (b) placing a desired amount of a nanomaterial suspension between and bridging the electrodes, (c) drying the nanomaterial suspension to form a nanostructure network, (d) annealing the network, and (e) electrochemically functionalizing the nanostructure network. The functionalization is performed by applying a nanoparticle solution to the nanostructure network, and then electrodepositing the nanoparticles on the surface of the nanomaterial in the nanostructure network.

In another aspect, this disclosure relates to a method of detecting the presence of specific gases in a gaseous environment or mixture (e.g., air), by the use of a gas sensor device comprising an electrochemically functionalized nanostructure network, of the type described above. Specifically, the method includes determining a baseline value of an electrical parameter (such as resistance) of the sensor device, exposing the device to a gaseous environment that may include the specific gas to be detected, and measuring any change in the electrical parameter value of the device after exposure to the gaseous environment. In one specific embodiment, the method is for detecting hydrogen, and the functionalization is provided by palladium nanoparticles. In another embodiment, the method is for detecting hydrogen sulfide gas and/or mercury vapor, and the functionalization is provided by gold nanoparticles. In yet another embodiment, the method is for detecting ammonia, nitrogen dioxide, and/or water vapor, and the functionalization is provided by doped polyaniline nanoparticles. In still another embodiment, the method is for detecting methane and/or ammonia, and the functionalization is provided by metal oxide (particularly tin oxide) nanoparticles.

DETAILED DESCRIPTION OF THE PREFERRED EMBODIMENTS

Figure 1:
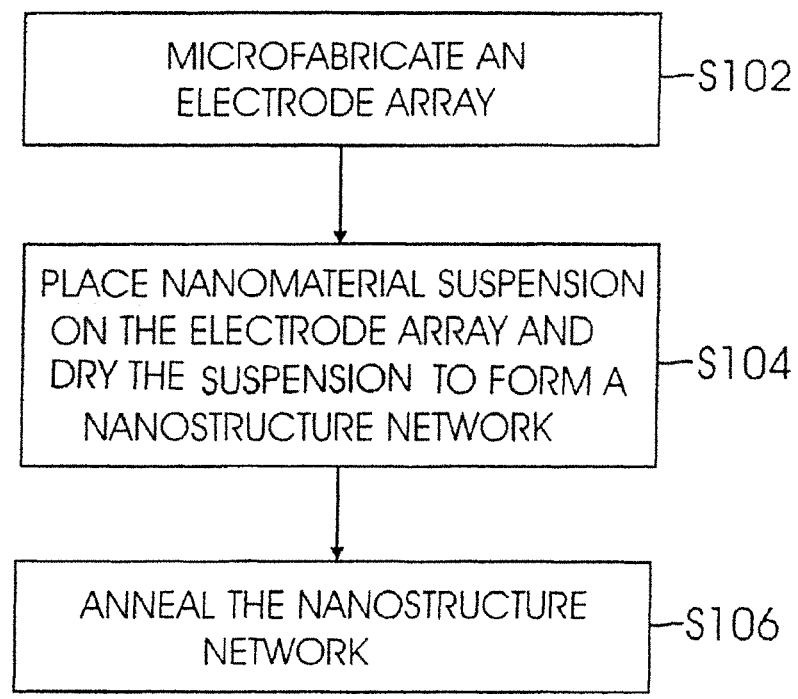
FIG. 1 is a flowchart of the steps in a process for making a nanostructure network chip for use in nanomaterial-based gas sensors, according to one aspect of the present disclosure.

The presently-disclosed nanomaterial-based gas sensors, in one aspect, provide a device for detecting or sensing a particular gas in a gaseous environment. In various embodiments, the device comprises a nanosensor chip that is used for the detection of a specific gas or gases (e.g., hydrogen, hydrogen sulfide, mercury vapor, ammonia, nitrogen dioxide, water vapor, or methane) in a gaseous environment that may include the specific gas or gases.

A gas sensor device, in accordance with the presently-disclosed embodiments, is a nanosensor chip that includes a nanostructure network formed on a substrate from a nanomaterial functionalized by any of several types of nanoparticles deposited on the nanomaterial. The specific material employed to functionalize the nanomaterial determines the specific gas to be detected. In specific embodiments, palladium (Pd) is used for detecting hydrogen, and gold (Au) is used for detecting hydrogen sulfide or mercury vapor, a doped polyaniline is used for detecting ammonia (NH$_3$), water vapor, and/or nitrogen dioxide (NO$_2$), and a metal oxide (particularly tin oxide) is used to detect methane and/or ammonia.

The sensing mechanism is based on a charge interaction between the molecules of a specified gas and the functionalization material (i.e., the nanoparticles) of the gas sensor. Specifically, the electrical properties of the nanosensor device, particularly its resistance, change from a predetermined baseline value upon exposure to a gaseous environment containing the specified gas as a result of the nanoparticles that functionalize the nanostructure accepting electrons from, or surrendering electrons to, the molecules of a specific gas to which the sensor is exposed, and to which the materials of the sensor are responsive. The change in a measured electrical property (particularly resistance) is measured or quantified, directly or indirectly. For example, a change in resistance may manifest itself as a change in current flowing through a circuit including the sensor or a change in the voltage drop across the sensor. The change in current or voltage is then measured and calibrated to a quantifiable gas concentration value. The magnitude of the change in the measured parameter establishes the concentration of the specified gas present in the system when compared to a baseline or calibration value of the measured parameter. These types of sensors, also referred to as chemiresistive sensors, have high sensitivity, low detection limits, fast response and recovery times, good reproducibility, good selectivity in the detection of gases, and long term stability within a wide temperature range.

The present disclosure further provides methods for producing nanomaterial-based gas sensors. In various embodiments, these methods provide a metal-based nanosensor chip, a doped polymer-based nanosensor chip, and a metal oxide-based nanosensor chip. A nanosensor chip in accordance with the present embodiments is formed by the electrochemical functionalization of a nanostructure network. The nanostructure network is formed from nanomaterials that may be nanowires, single walled carbon nanotubes (SWNTs) or other nanomaterials. The functionalization may involve metal, doped polymer, or metal oxide nanoparticles that are electrodeposited on the nanostructure network to form the nanosensor chip. The metal may be palladium (Pd) if hydrogen is to be detected, and it may be gold (Au) if hydrogen sulfide or mercury vapor is to be detected. The polymer may be polyaniline (PANI) and the dopant may be camphor-sulfonic acid (CSA) (for RH-independent ammonia and nitrogen dioxide detection), chloride (Cl⁻) (for ammonia, nitrogen dioxide, and water vapor detection), perchlorate ($ClO_4^-$), acrylic acid ($C_3H_4O_2$), tetraethylammonium perfluorooctane sulfonate (TEAPFOS) or para-toluene sulfonic acid ($CH_3C_6H_4SO_3H$), the last four being useful for ammonia and water vapor detection. The metal oxide may be tin oxide ($SnO_2$) for ammonia or methane detection. These functionalized nanostructure networks have broader selectivity and further improved sensitivity compared to unfunctionalized nanostructures. Those of ordinary skill in the art will appreciate that there are infinitely many combinations of nanostructures and dopants that may be used in the present embodiments. Therefore, the specific embodiments disclosed herein should be viewed as examples only, and not as limitations.

FIG. 1 shows the process steps for the fabrication of a nanomaterial-based electrode network (also referred to as a nanostructure network) for a nanosensor chip according to the present embodiments. Some of these process steps are illustrated in FIGS. 2A, 2B, 4A and 4B.

Figure 2A:
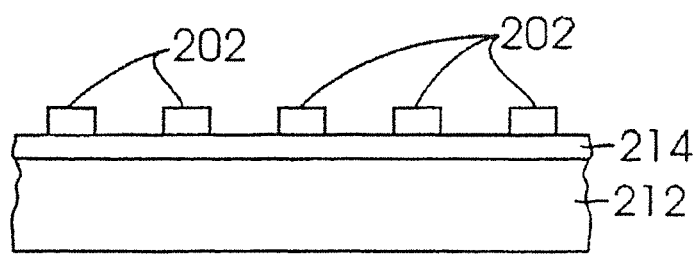
FIG. 2A is a schematic, front elevation view of a chip with an electrode array that is made in the method shown in FIG. 1.
Figure 2B:
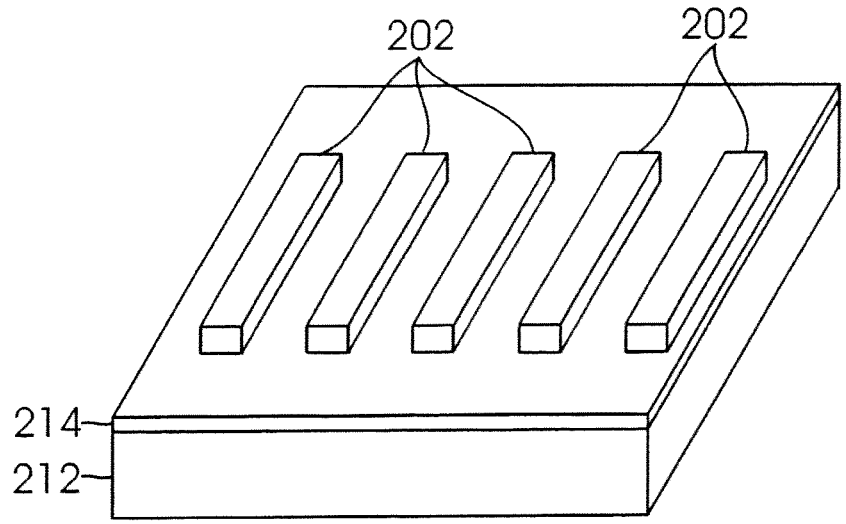
FIG. 2B is a schematic, top perspective view of the chip of FIG. 2A.

In step S102, an array of conductive electrodes 202 (as shown in FIGS. 2A and 2B) is formed on a substrate 212 that is preferably made of a semiconductive material, such as silicon, for example. The electrodes 202 are preferably formed on an insulative passivation layer 214 that is formed by standard techniques, such as chemical vapor deposition (CVD), on the substrate 212. The passivation layer 214 may be made of materials selected from the oxides of aluminum, magnesium, copper, silicon, and titanium, as well other passivation materials that are known in the art. In one exemplary embodiment, in which the substrate 212 is silicon, the passivation layer 214 may advantageously comprise a silicon dioxide ($SiO_2$) layer of approximately 1 micron in thickness applied to the substrate 212 by CVD.

The electrodes 202 may advantageously be formed in a substantially parallel array on the passivation layer 214, using conventional photolithography, screen printing, electrodeposition, or standard sintering techniques, for example. The electrodes 202 may be formed of metals that do not oxidize easily, such as, for example, nickel, gold, platinum, palladium or other metals known in the art to be suitable for this application. The electrodes 202 may be in the range of 1 μm to 10 μm in width, such as, for example, 3 μm. The electrodes 202 are separated by a gap having a width in the range of several hundred nanometers to more than 100 μm. In one embodiment, the gap is between 1 μm and 10 μm, such as, for example, 3 μm.

In one exemplary embodiment, the areas on which the electrodes 202 are to be formed are defined on the passivation layer 214 by photolithography, and an adhesion layer (not shown) is then applied. The adhesion layer may be titanium, chromium, tungsten, nickel, tin, vanadium, or any other suitable material known in the art. In the exemplary embodiment, a gold layer (not shown) approximately 3,000 Å thick is electron beam evaporated onto the adhesion layer, and the electrodes 202 are then formed by conventional chemical lift-off techniques.

In step S104, a droplet 400 (FIG. 4A) of nanomaterial suspension is placed in the gaps between the electrodes 202 so as to bridge the gaps between adjacent electrodes 202, and then dried. The droplet 400 may have a volume in the range between 0.1 μL-1.0 μL. In one embodiment, the nanomaterial may be a semiconducting nanomaterial selected from the group consisting of single-walled carbon nanotubes (SWNTs), multi-walled carbon nanotubes (MWNTs), silicon nanowires, zinc oxide nanostructures, tin oxide nanowires, indium oxide nanowires, carbon boride nanotubes, carbon nitride nanotubes, and other nanomaterials, such as the general $B_xC_yN_z$ nanotube structures. SWNTs are preferred, because they provide several advantages. For example, because all the carbon atoms in SWNTs are exposed to the outer surface, the surface area per unit volume is maximized. Further, the specific helicity of the carbon atom structure in SWNTs can be selected to provide the desired semiconductive characteristics. For simplicity, many of the examples provided herein refer to SWNTs. However, those of ordinary skill in the art will appreciate that the disclosed embodiments are not limited to the use of SWNTs.

The nanomaterial suspension is formed by dispersing the nanomaterial in a solvent such as water, dimethyl formamide (DMF), or any other suitable solvent known in the art. In one exemplary embodiment, SWNTs having a —COOH group (such as SWNT-COOH 80-90% purity, produced by Carbon Solution, Inc. of Riverside, Calif.) are ultrasonically dispersed in DMF in a concentration of 0.5 μg/mL, although in other embodiments the concentration of the suspension may be in the range of about 0.01 μg/mL to 1.0 μg/mL or greater. DMF is an advantageous solvent, because the amide group of that compound can attach to the surface of the SWNTs, thereby facilitating a uniform suspension of the SWNTs. In the exemplary embodiment, a 0.05 μL drop of the SWNT/DMF suspension is deposited in the electrode gaps by a micro-syringe or other suitable device.

Figure 4A:
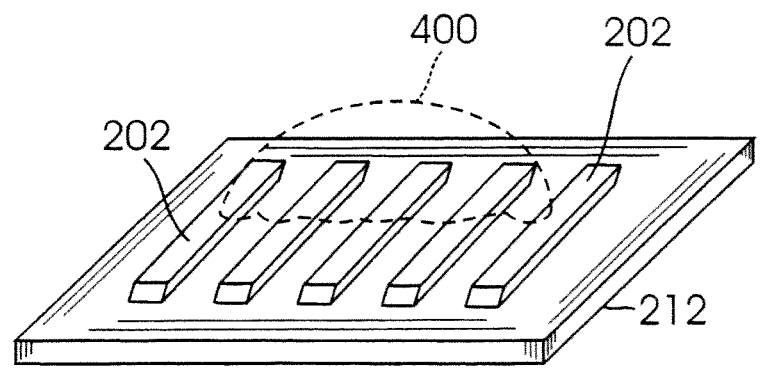
FIG. 4A is a schematic, top perspective view of a nanostructure network chip with an electrode array and a droplet of a nanomaterial suspension, according to one embodiment of the method shown in FIG. 3.
Figure 4B:
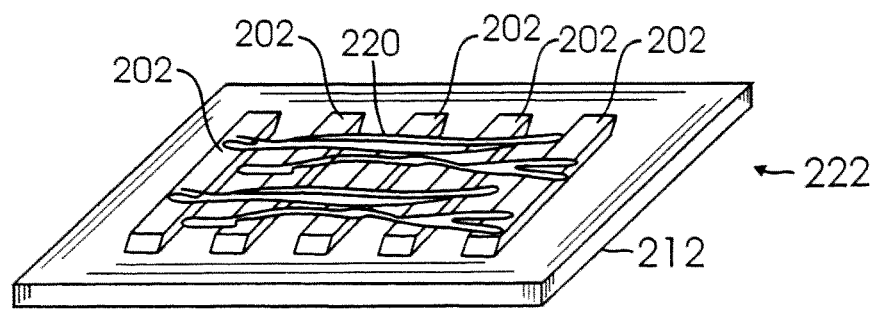
FIG. 4B is a schematic, top perspective view of a nanostructure network chip constructed according to one embodiment of the method shown in FIG. 3.

The nanomaterial suspension is dried by evaporation of the solvent to form a nanostructure network 222 comprising an array of electrodes 202 connected by the nanomaterial bridges 220, as shown in FIG. 4B. The solvent evaporation may be performed at room temperature or at an elevated temperature. To remove solvent residue and to reduce contact resistance between the nanomaterial and the electrodes 202, annealing is performed in step S106. The annealing may be performed by heating the substrate 212, with the electrodes 202 and nanomaterial bridges, to about 200° C.-600° C. for at least about 15 minutes in an inert or reducing environment. In one example embodiment, the annealing step is performed at 350° C. in an argon atmosphere for about 60 minutes. The dried and annealed nanomaterial bridges 220 traverse the gaps between adjacent electrodes 202. Variations in the concentration of the SWNTs in the DMF solution or variations in the size of the droplet 400 can produce corresponding variations in the density of the nanomaterial in the bridges 220.

Figure 3:
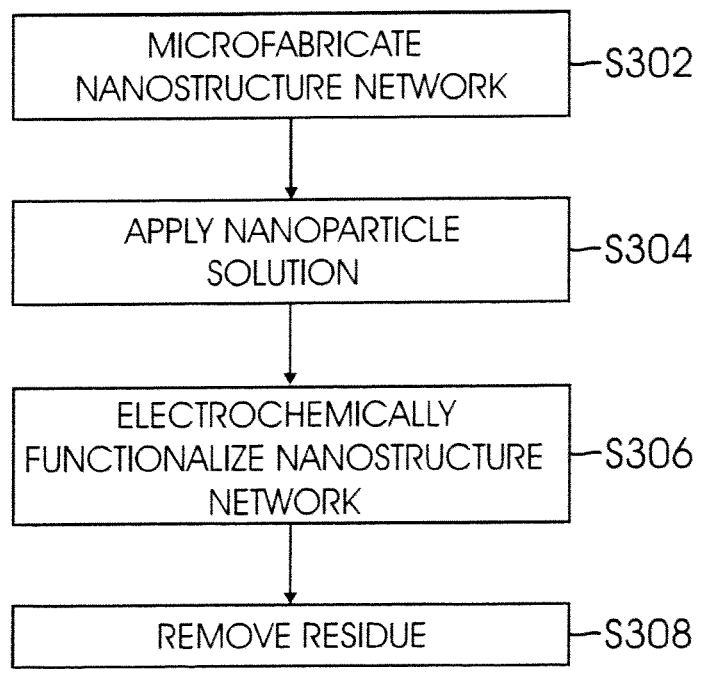
FIG. 3 is a flowchart of the steps in a process for producing a nanomaterial-based gas sensor on a nanostructure network of the type illustrated in FIGS. 2A and 2B, according to an aspect of the present disclosure.
Figure 4C:
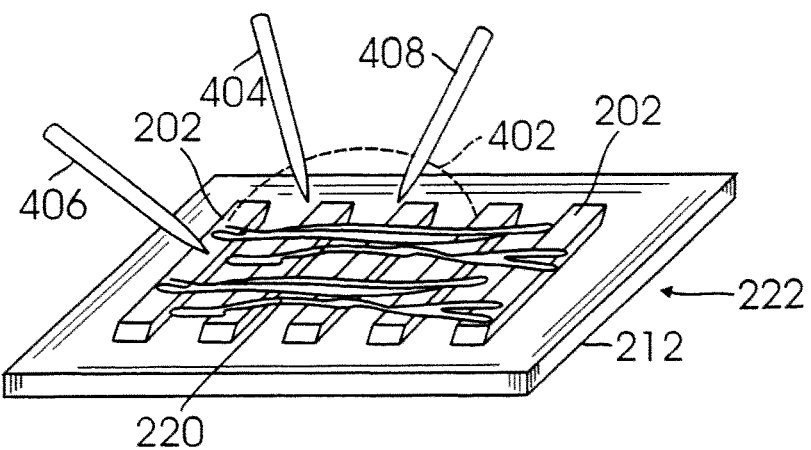
FIG. 4C is a schematic, top perspective view of the nanostructure network chip of FIG. 4B, illustrating the step of electrodepositing nanoparticles on the nanomaterial in accordance with one embodiment of the method shown in FIG. 3.
Figure 4D:
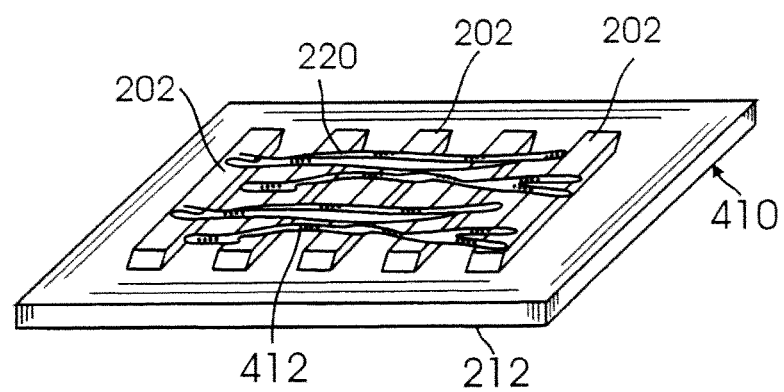
FIG. 4D is a schematic, top perspective view of a nanomaterial-based gas sensor in accordance with one aspect of the present disclosure.

The nanostructure network 222 is then functionalized by the electrodeposition of nanoparticles to form a gas-detecting nanosensor. In various embodiments, as described more fully below, the nanoparticles may be elemental metal, doped polymer, or metal oxides. FIG. 3 shows the steps of forming a nanosensor on a nanostructure network 222, of the type described above and shown in FIG. 4B. Some of the process steps of FIG. 3 are illustrated in FIGS. 4C and 4D. Thus, as shown in FIG. 3, in step S302, a nanostructure network 222 is formed by following the process steps of FIG. 1. In one exemplary embodiment, the nanostructure network 222 comprises SWNTs as the nanomaterial bridge 220 connecting the electrodes 202, as described above.

In step S304 of the flowchart of FIG. 3, a nanoparticle solution is applied to the nanostructure network 222 to cover the nanomaterial bridges 220. In embodiments in which the nanoparticles are elemental metal, the solution is a metal plating solution containing metal ions. Step 306 is the step of functionalizing the network 222. For metal nanoparticles, the functionalization is performed by the electrodeposition of metal nanoparticles on the nanomaterial bridges 220. These steps are shown in FIG. 4C, where an electrochemical cell is formed on a nanostructure network by a droplet 402 (e.g., about 3 μL) of metal plating solution, such as a metal electrolyte solution. A reference electrode 404, a working electrode 406, and a counter electrode 408 are inserted in the plating solution droplet 402. In one exemplary embodiment, a nanostructure network electrode 202 is employed as the working electrode 406, one or more platinum wires serve as the counter electrode 408, and an Ag/AgCl wire is used as the reference electrode 404. In another exemplary embodiment, a gold wire is used for the working electrode 406, a platinum wire is used for the counter electrode 408, and an Ag/AgCl wire is used as the reference electrode 404.

The metal plating solution may be a palladium-based solution (for the detection of hydrogen), or a gold-based solution (for the detection of hydrogen sulfide and/or mercury vapor). Those of ordinary skill in the art will appreciate that solutions based on other metals may also be used, and that the metal may be chosen on the basis of the gas or vapor to be detected. In one exemplary palladium embodiment, a Pd plating solution comprises 10 g/L of $Pd(NH_2)(NO_2)_2$ and 100 g/L ammonium sulfamate. The pH is adjusted to about 8.0 by the addition of sulfamic acid and sodium hydroxide to prevent the dissolution of the chromium passivation layer 214 (FIG. 2A) in an acidic environment. An exemplary gold plating solution comprises 1.25 g/L-2 g/L potassium gold cyanide, 7.5 g/L potassium cyanide, and 15 g/L of dipotassium phosphate. The electrodeposition may advantageously be performed at ambient pressure and at temperatures in the range of about 15° C.-45° C., including at room temperature (20° C.-25° C.).

Though the electrodeposition method as defined herein uses a three electrode configuration, those of skill in the art will appreciate that a two electrode configuration for electrodeposition may be used instead. In a two electrode configuration, the nanostructure network 222, including gold electrodes 202, can function as the working electrode 406 in place of the discrete wire working electrode 406 shown in FIG. 4C.

FIG. 4D shows a nanosensor chip 410 having a functionalized nanostructure 412 comprising the SWNT nanomaterial bridge 220 "decorated" by the electrodeposition of metal nanoparticles, as described above. In step S308 (FIG. 3), the nanosensor chip 410 is rinsed with deionized water to remove any impurities, such as plating solution residues.

The functionalized nanosensor chip 410 thus formed can be used as a sensing electrode in a chemiresistive sensor. As mentioned above, a palladium-based nanosensor chip may be used for the detection of hydrogen ($H_2$), while a gold-based nanosensor chip may be used for the detection of hydrogen sulfide ($H_2S$) and/or mercury (Hg) vapor. Those of ordinary skill in the art will appreciate that these metals may also be used to detect other gases, and that other metals may be used to detect these or other gases.

In the above-described electrodeposition method, the final nanoparticle size and the density of metal deposition can advantageously be controlled by varying the deposition potential (i.e., voltage) applied, and/or the duration (i.e. the charge) of the deposition. Variations in these deposition parameters define the extent of metal nanoparticle deposition on the nanostructure network, as detailed below.

FIGS. 5A-5D and 6A-6D graphically illustrate exemplary experimental results that, although obtained under a particular set of experimental conditions, serve to demonstrate the relationship between deposition parameters (potential and charge density) and deposition results (nanoparticle size and density). The data from these graphs may be used to optimize deposition parameters for particular applications. Thus, for example, the diameter and density of the deposited nanoparticles may be selected to avoid excessive contact between the deposited nanoparticles.

Figure 5A:
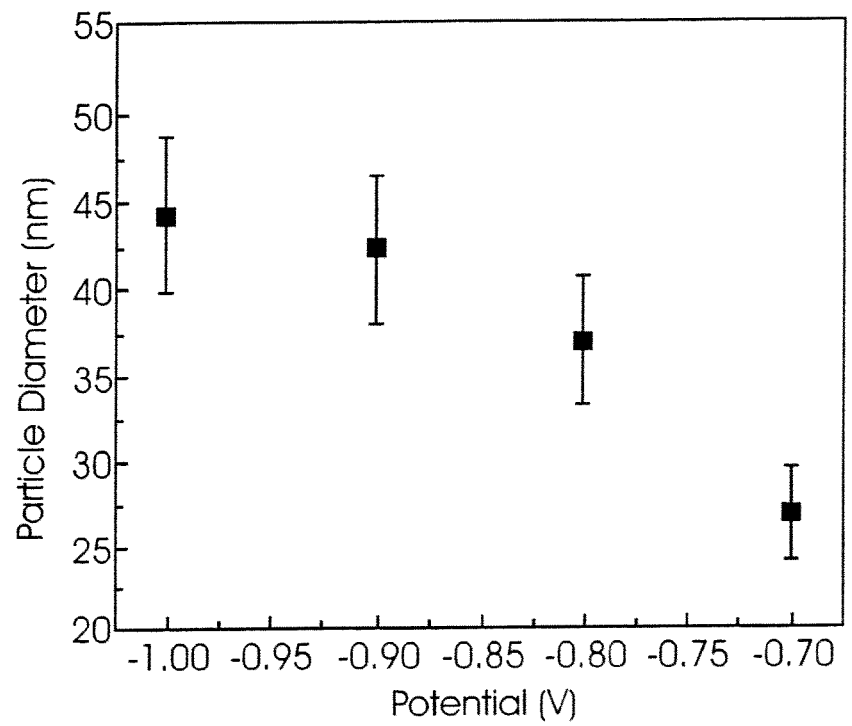
FIG. 5A is a graph showing a relationship between deposition potential and nanoparticle diameter for the deposition of palladium nanoparticles on SWNTs under a particular set of experimental conditions.
Figure 5B:
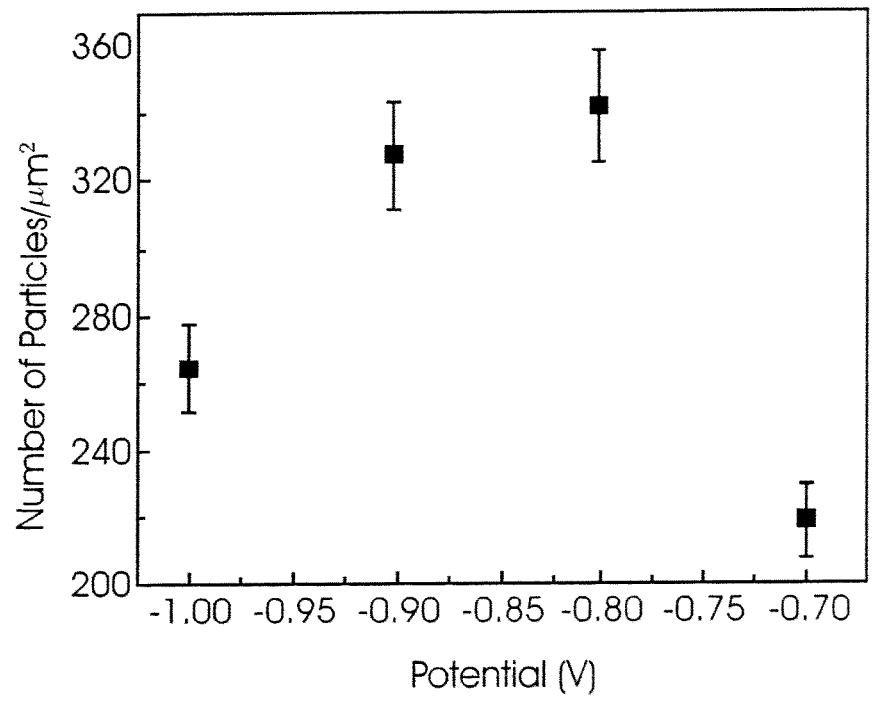
FIG. 5B is a graph showing a relationship between deposition potential and nanoparticle density for the deposition of palladium nanoparticles on SWNTs under the set of experimental conditions used to obtain relationship illustrated in the graph of FIG. 5A.
Figure 5C:
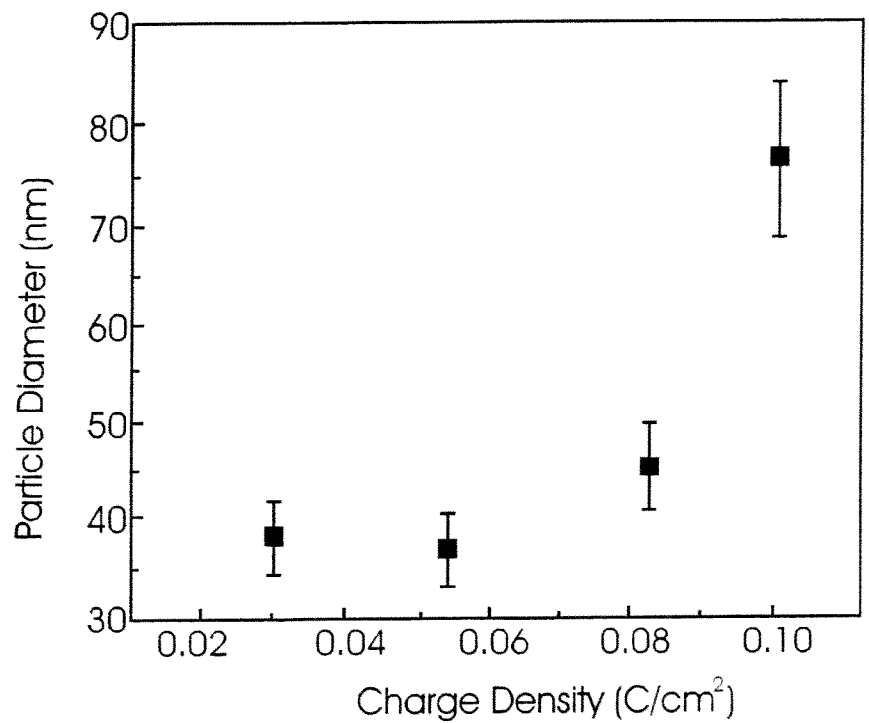
FIG. 5C is a graph showing a relationship between deposition charge density and nanoparticle diameter for the deposition of palladium nanoparticles on SWNTs under a particular set of experimental conditions.
Figure 5D:
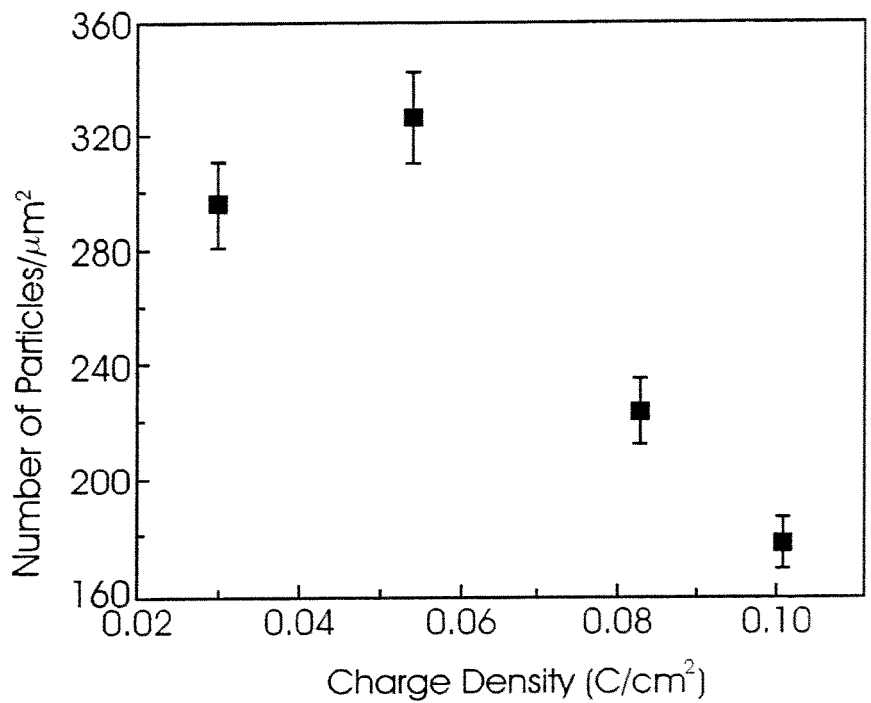
FIG. 5D is a graph showing a relationship between deposition charge density and nanoparticle density for the deposition of palladium nanoparticles on SWNTs under the set of experimental conditions used to obtain relationship illustrated in the graph of FIG. 5C.

As shown in FIGS. 5A and 5B, for palladium nanoparticles, average particle diameter decreases gradually as the applied potential is varied from −1.00 V to about −0.70 V, while nanoparticle density increases markedly as the applied potential is varied from −1.00 V to about −0.80 V, then decreases dramatically at −0.70 V. FIG. 5C shows that nanoparticle diameter is relatively constant with increasing charge density, until a charge of about 0.08 Coulombs/cm$^2$ is reached, at which point particle diameter begins to increase dramatically with charge, indicating that at about 0.08 Coulombs/cm$^2$ the nanoparticles begin to coalesce with neighboring nanoparticles. FIG. 5D shows that nanoparticle density increases with charge as the charge density is increased from about 0.03 Coulombs/cm$^2$ to about 0.06 Coulombs/cm$^2$, and then markedly decreases as the charge density increases to about 0.10 Coulombs/cm$^2$, likewise indicating a coalescing of nanoparticles above a certain charge threshold. The charge dependent studies were carried out at −0.8 V.

Figure 6A:
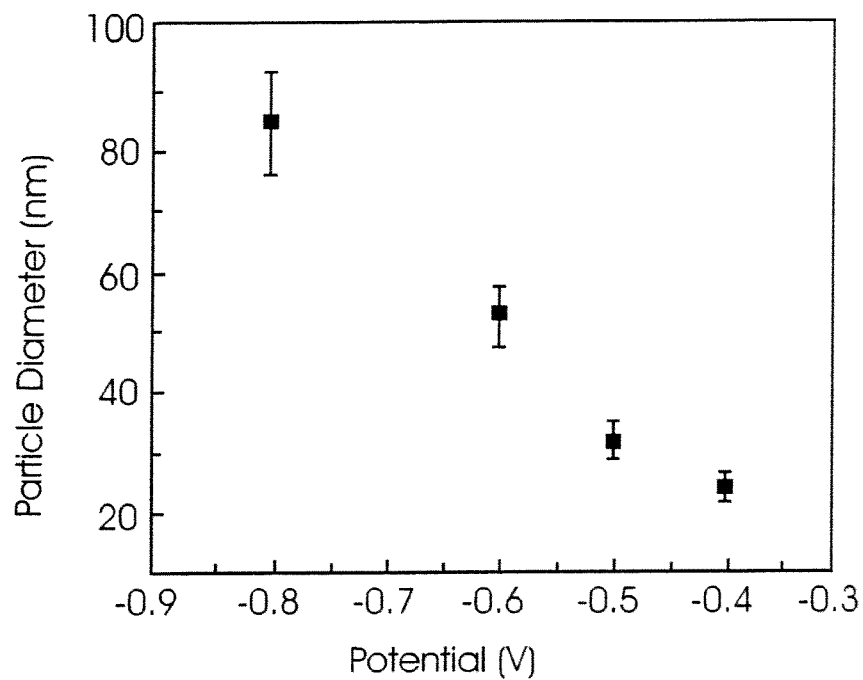
FIG. 6A is a graph showing a relationship between deposition potential and nanoparticle diameter for the deposition of gold nanoparticles on SWNTs under a particular set of experimental conditions.
Figure 6B:
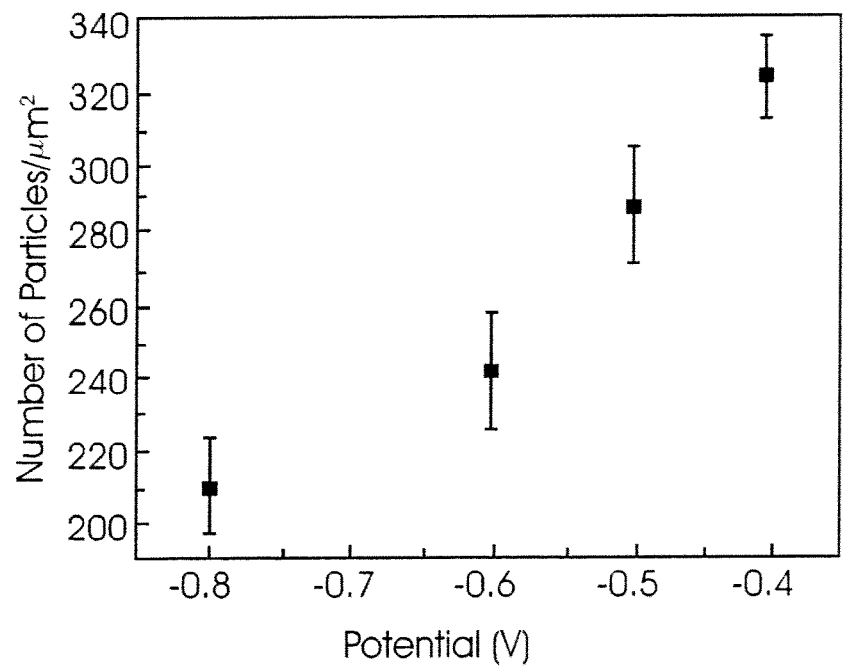
FIG. 6B is a graph showing a relationship between deposition potential and nanoparticle density for the deposition of gold nanoparticles on SWNTs under the set of experimental conditions used to obtain relationship illustrated in the graph of FIG. 6A.
Figure 6C:
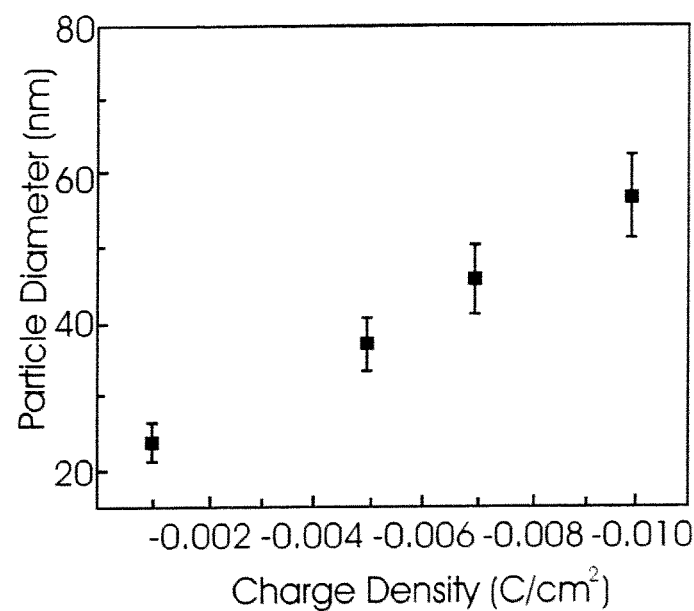
FIG. 6C is a graph showing a relationship between deposition charge density and nanoparticle diameter for the deposition of gold nanoparticles on SWNTs under a particular set of experimental conditions.
Figure 6D:
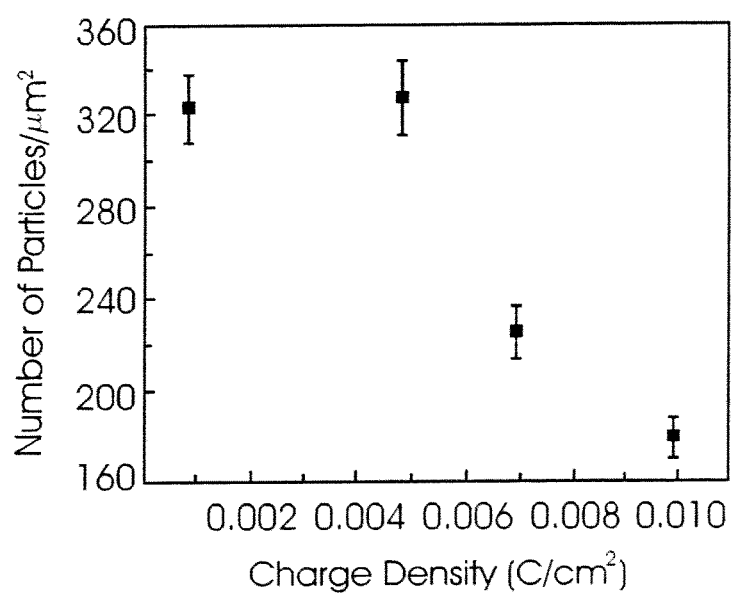
FIG. 6D is a graph showing a relationship between a deposition charge density and nanoparticle density for the deposition of gold nanoparticles on SWNTs under the set of experimental conditions used to obtain relationship illustrated in the graph of FIG. 6C.

FIGS. 6A-6D show how gold nanoparticle size and density vary with the deposition potential (i.e., voltage) applied, and/or the duration (i.e. the charge) of the deposition. FIG. 6A shows that gold nanoparticle diameter decreases substantially linearly as the deposition potential is varied from about −0.8 V to about −0.4 V, while FIG. 6B shows substantially linearly increasing nanoparticle density as the deposition potential is varied in the same range. FIG. 6C shows that gold nanoparticle diameter increases substantially linearly with charge density throughout the measured range, while FIG. 6D shows that gold nanoparticle density begins to fall off dramatically at charge densities above about 0.05 Coulombs/cm$^2$.

In accordance with another aspect of the presently disclosed technology, the above-described nanosensor devices are employed as gas sensors in a method of detecting the presence of a particular gas in a gaseous environment, such as air. The nanosensor device may comprise a substrate having at least a pair of conductive electrodes formed thereon and defining a gap therebetween, with a functionalized nanomaterial bridge connecting the electrodes across the gap to form a nanostructure network. Specifically, in one exemplary embodiment, the method may be for the detection of hydrogen using the above-described nanosensor device, with palladium nanoparticles employed as the functionalization material. In another exemplary embodiment, the method may be for the detection of hydrogen sulfide and/or mercury vapor using a sensor with gold nanoparticles employed for the functionalization of the nanomaterial. In either embodiment, the method may further comprise the measurement of a baseline or nominal value of a selected electrical parameter of the sensor, the exposure of the sensor to a gaseous environment that may include the selected gas to be detected, and the measurement of the value of the selected electrical parameter after the exposure.

In each embodiment of the above-described gas detection methods, the value of an electrical characteristic or parameter (such as resistance) of the sensor is measured, both before and after exposure, by placing the sensor in an electrical circuit in which the value of the characteristic or parameter can be measured either directly or indirectly. Resistance, for example, may be measured by placing the chip in a circuit in which the voltage drop across the chip is measured, given a constant current.

Several embodiments of the above-described gas sensors were prepared for use in gas detection studies. In preparation for these studies, the electrodes of each sensor were wire bonded and each sensor was connected in series with a load resistor. The circuit was subjected to a fixed 1V DC potential, and the electrical resistance of the sensor was determined from continuously monitoring the voltage across the resistor and applying Ohm's law. A 3.62 cm$^3$ sealed glass chamber with gas inlet and outlet ports for gas flow-through was positioned over the sensor chip. All experiments were conducted with known concentrations of analyte diluted in air at a total gas flow of 400 standard cubic centimeters per minute. Humidity control was generated by bubbling dry air through a bubbler column. The gas flow rates were regulated by mass flow controllers (Alicat Scientific Incorporated. Tucson, Ariz.). A custom Labview computer program was developed to continuously control and monitor the voltage of the circuit using Fieldpoint analog input and output modules (National Instruments, Austin. Tex.). All sensing experiments were conducted at ambient conditions. In all experiments, the sensors were first exposed to air to obtain a baseline, and then to a desired concentration of analyte, and then back to air to complete one cycle.

Figure 7A:
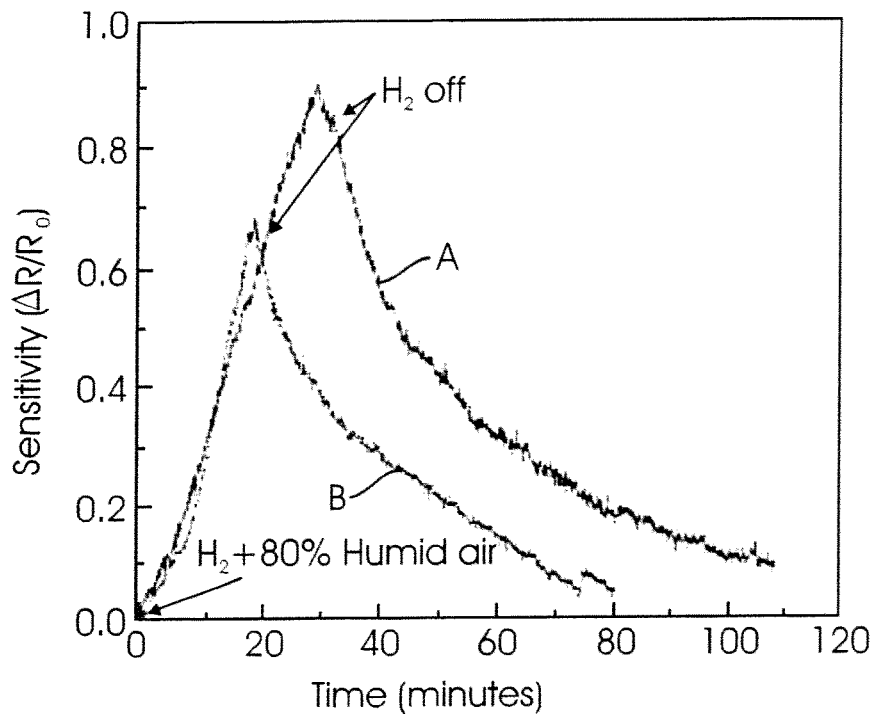
FIG. 7A is a graph showing sensitivities of palladium-based gas sensors having two different densities of palladium nanoparticles.

FIG. 7A shows the sensitivities of Pd-based nanosensor devices having two different palladium nanoparticle densities, when exposed to 200 ppm$_v$ hydrogen in air. Curve A represents a sensor with a nanoparticle density of about 330 particles/µm$^2$, obtained at an applied potential of −0.90V (FIG. 5B) and at a charge density of about 0.05 Coulombs/cm$^2$ (FIG. 5D). Curve B represents a sensor with a nanoparticle density of about 220 particles/µm$^2$, obtained at an applied potential of −0.70V (FIG. 5B) and at a charge density of about 0.10 Coulombs/cm$^2$ (FIG. 5D). Within about 18-30 minutes after exposure to hydrogen, the sensitivity of both sensors increases to a peak value. When exposure to hydrogen ceases, the sensitivity slowly returns to its original value. The sensitivity (defined as the change in resistance divided by the baseline resistance of the sensor in the carrier gas, i.e., air with 80% relative humidity) shows a significant decrease with increasing charge density. This result follows from the discussion of FIG. 5D, supra, which shows that nanoparticle density decreases with increasing charge density at values above about 0.06 Coulombs/cm$^2$, where coalescing of nanoparticles into a palladium film begins to occur.

Figure 7B:
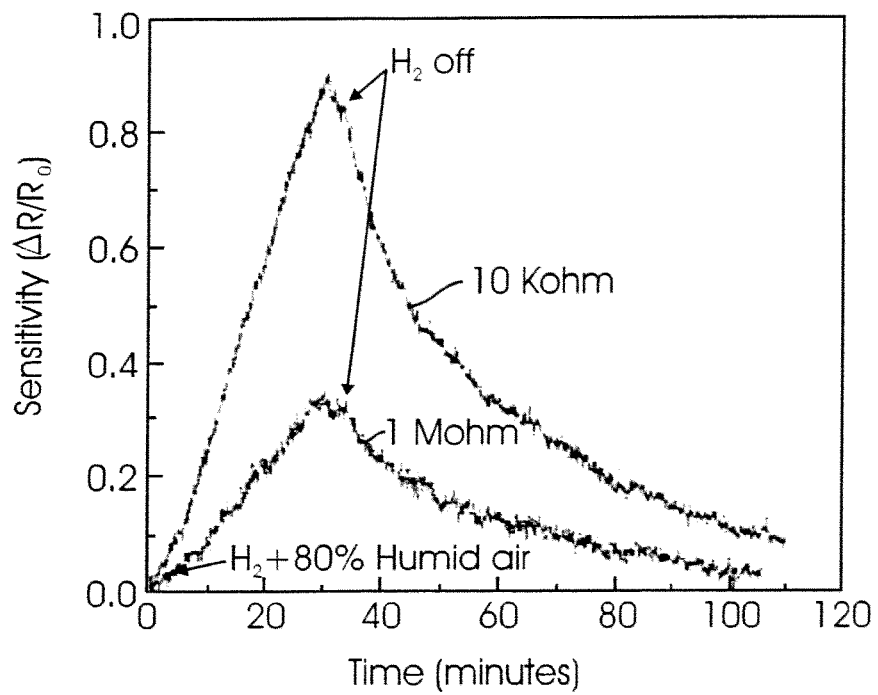
FIG. 7B is a graph showing a variation in sensitivity with varying baseline network resistance for palladium-based gas sensors according to the present invention.

FIG. 7B shows an increase in the sensitivity of the Pd-based nanosensor chip with decreasing baseline SWNT nanostructure network resistance. A nanostructure network having a greater number of interconnects provides lower resistance, which results in increased available surface area for the sensing function and therefore better sensing performance. As indicated by the results evidenced in FIG. 7B, sensitivity was improved at a baseline resistance of about 10 K-ohm.

Figure 8:
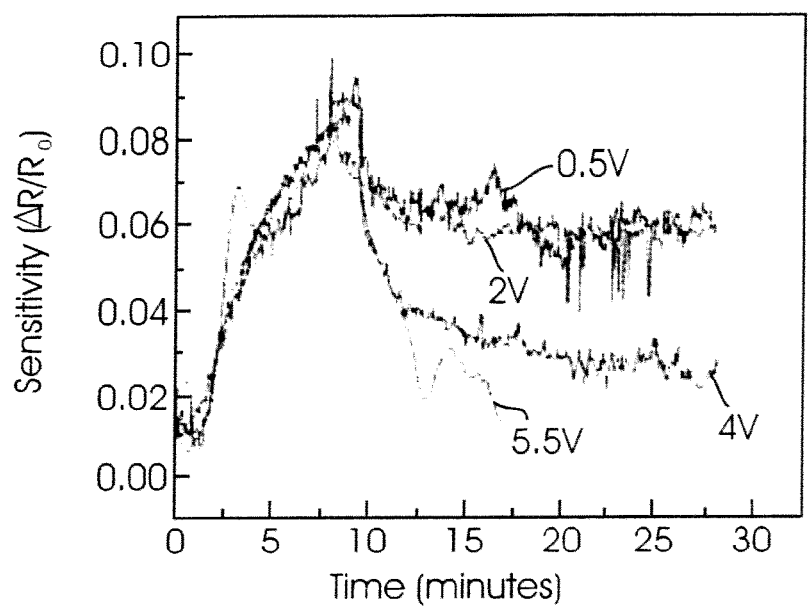
FIG. 8 is a graph showing the sensitivity-versus-exposure time for the exposure to 20 $ppb_v$ of $H_2S$ at different potentials applied across a gold-based gas sensor in accordance with one aspect of the present disclosure.

FIG. 8 shows the sensing behaviors of a gold-based nanosensor with varying potential applied across the nanostructures. At applied bias voltages between the electrodes varying from 0.5V to 5.5V, peak sensitivity is reached about 8-10 minutes after exposure to hydrogen sulfide, but the fall-off in sensitivity is more rapid with bias voltages at the higher end of the range. Further, although sensitivity does not appreciably change with applied bias voltage, recovery time markedly decreases at higher operating bias voltages.

Figure 9:
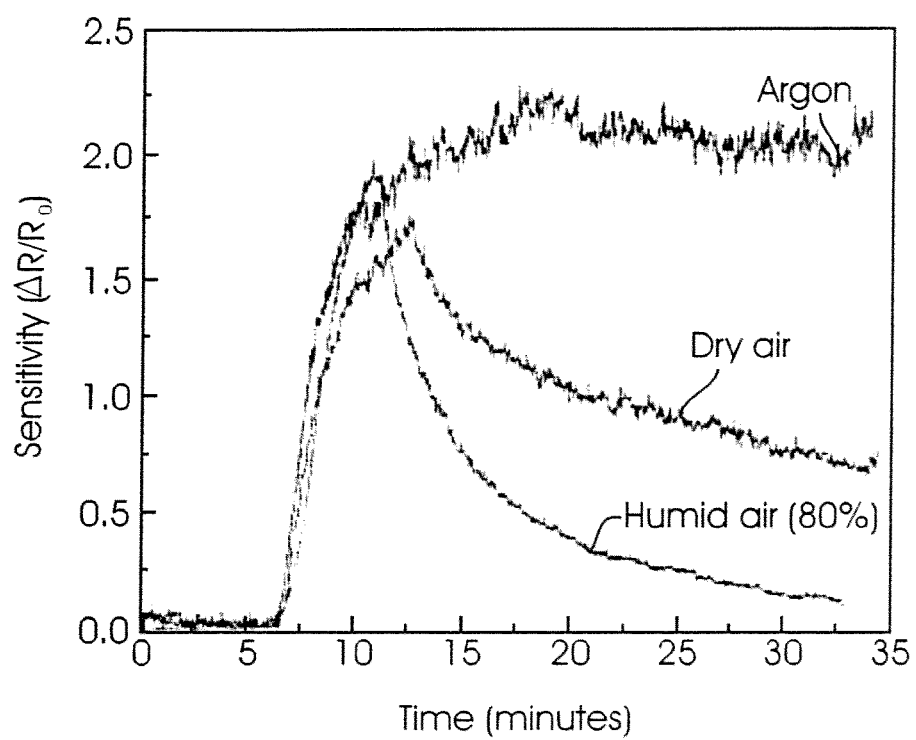
FIG. 9 is a graph showing the sensitivity-versus-exposure time for the exposure to 400 ppm$_v$ of hydrogen in the presence of humid air, dry air, and argon, respectively, of a palladium-based gas sensor in accordance with one aspect of the present disclosure.

FIG. 9 shows the sensitivity of a Pd-based nanosensor at ambient conditions when the carrier gas is, respectively, argon, dry air, and humid air (80% relative humidity). For dry air, the sensor shows a prompt resistance change upon exposure to hydrogen (400 ppm). However, a relatively long period of time (typically more than one hour) is needed for complete recovery. The presence of moisture in the air does not appreciably change the response to hydrogen exposure, but it markedly decreases the recovery time. With argon as the carrier gas, there is little or no recovery. Although not represented in a graph herein, the sensitivity and recovery time of gold-based nanosensors in accordance with the present embodiments are likewise affected by humidity. In contrast to the present palladium-based nanosensors, the sensitivity of gold-based nanosensor chips generally decreases, and recovery time generally increases, as humidity increases.

Figure 10A:
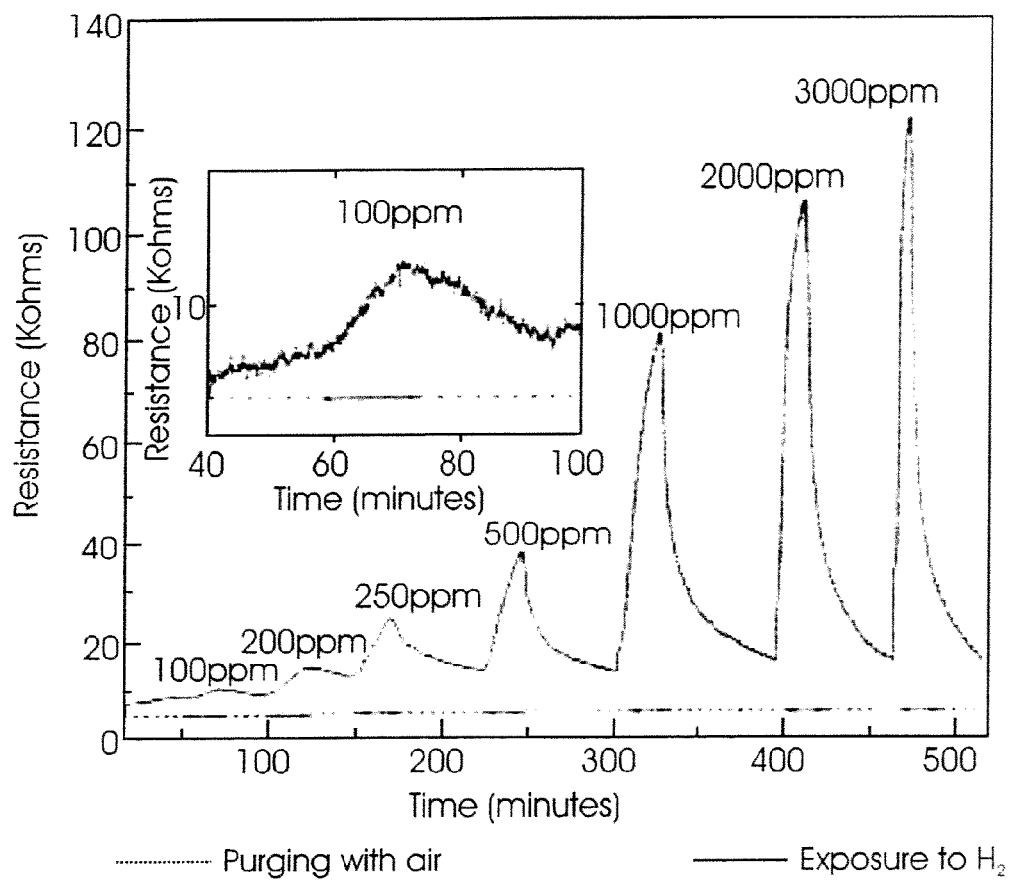
FIG. 10A is a graph showing the response (resistance-versus-time) of a palladium-based gas sensor, in accordance with one embodiment of the present invention, in response to the exposure of the sensor to varying concentrations of hydrogen in 80% relative humidity air at room temperature and ambient pressure.
Figure 10B:
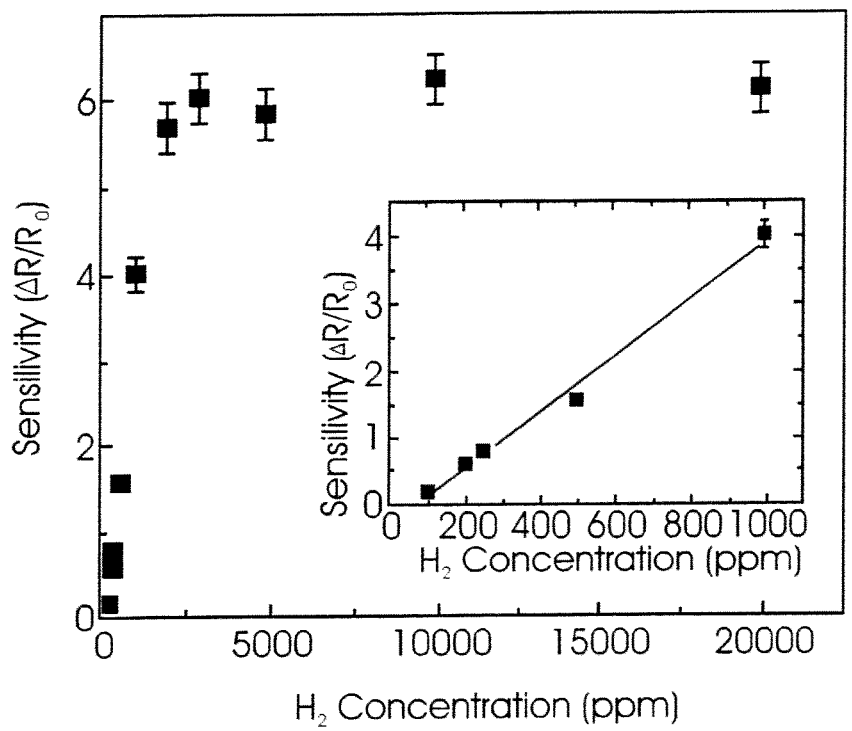
FIG. 10B is a graph showing the relationship between the sensitivity of a palladium-based gas sensor, in accordance with one aspect of the present disclosure, and the concentration of hydrogen gas to which the sensor is exposed.
Figure 10C:
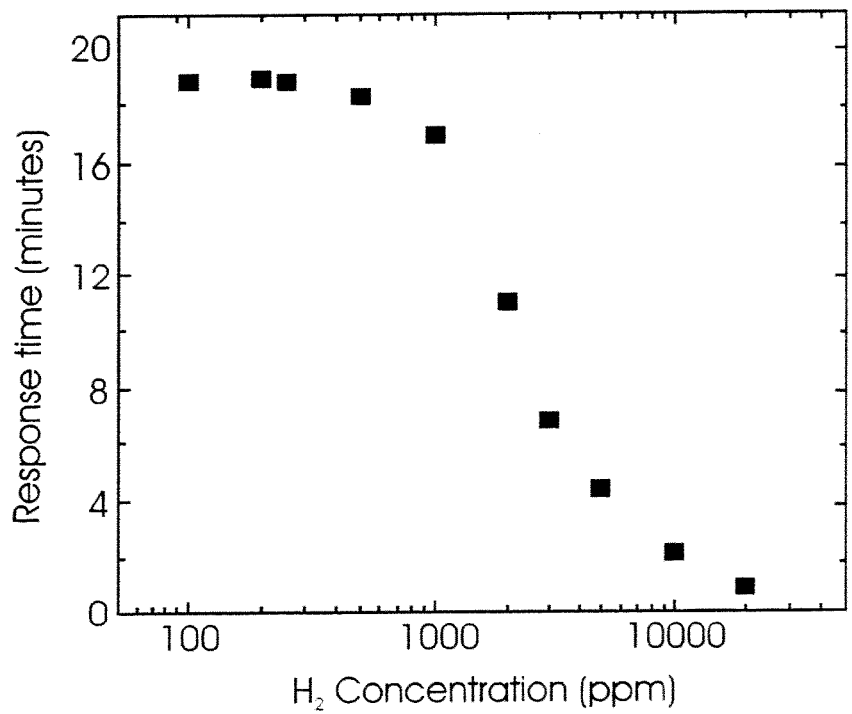
FIG. 10C is a graph showing the response time of a palladium-based gas sensor, in accordance with one aspect of the present disclosure, as a function of hydrogen gas concentration.
Figure 10D:
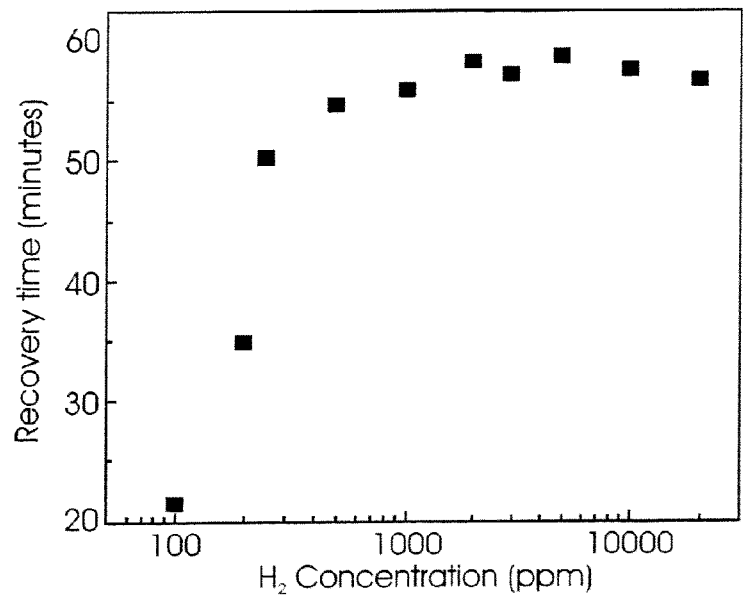
FIG. 10D is a graph showing the recovery time of a palladium-based gas sensor, in accordance with one aspect of the present disclosure, as a function of hydrogen gas concentration.

FIG. 10A shows the resistance increase of a 10 K-ohm Pd-based nanosensor resulting from hydrogen exposure in 80% relative humidity air at room temperature and ambient pressure, with hydrogen concentrations ranging from 100 ppm, to 3.000 ppm$_v$. In each case, the sensor resistance promptly reaches a peak value during exposure to hydrogen, and returns to its baseline when the hydrogen feed is discontinued and a purging airflow is supplied. With reference to FIG. 10B, the sensitivity of the sensor shows a linear relationship for hydrogen concentrations ranging from 100 ppm$_v$ to 1,000 ppm$_v$ (FIG. 10B inset), and sensor saturation is evident above 3,000 ppm$_v$. The response time, defined as the time required for the sensor to reach 90% of the final signal value, does not vary much in the linear range of detection, but shows a rapid decrease at concentrations above 1,000 ppm, in the saturation regime (FIG. 10C). At room temperature, the response time is about 18 minutes for hydrogen concentrations up to 300 ppm$_v$, and it decreases to about 7 minutes at 3,000 ppm$_v$. Complete recovery is observed for the sensors at all concentration ranges, and the recovery time varies from about 20 minutes at 100 ppm$_v$ to about 55 minutes at 1.000 ppm$_v$ (FIG. 10D).

Figure 11A:
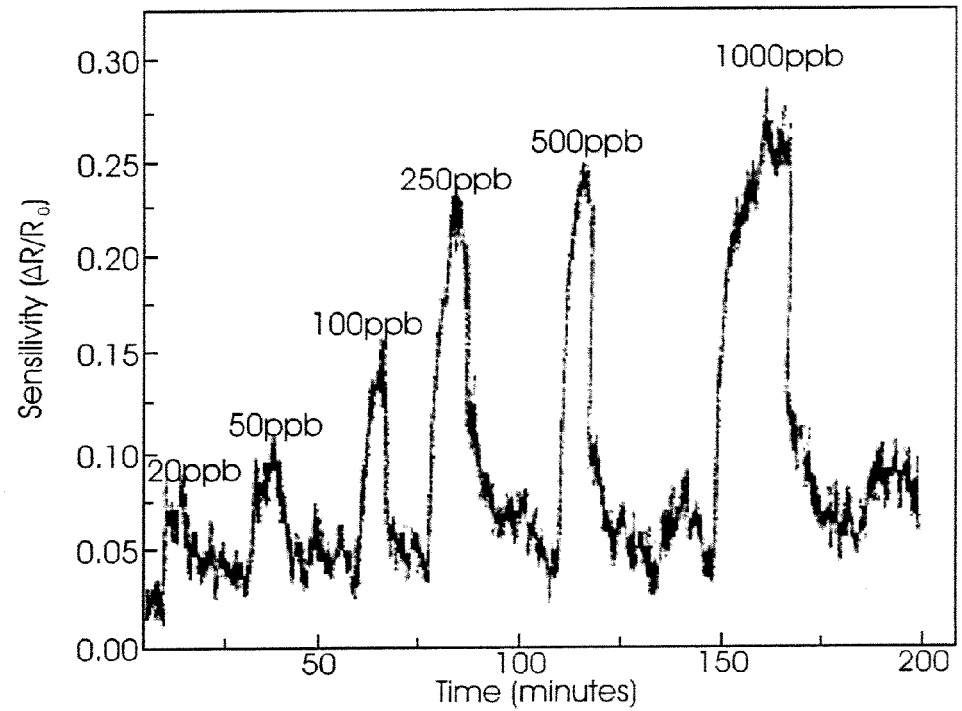
FIG. 11A is a graph showing the sensitivity of a gold-based gas sensor, in accordance with one aspect of the present disclosure, to different concentrations of hydrogen sulfide in dry air as a function of time.
Figure 11B:
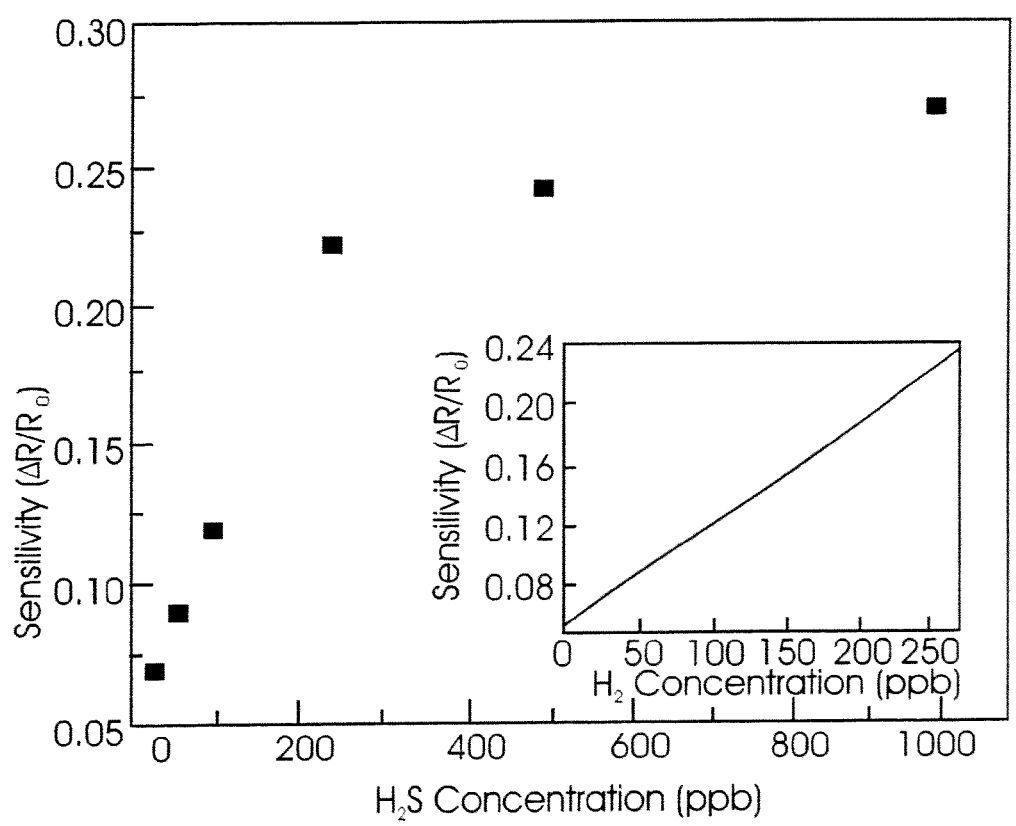
FIG. 11B is a graph showing the sensitivity of a gold-based gas sensor, in accordance with one aspect of the present disclosure, as a function of the concentration of hydrogen sulfide to which the sensor is exposed.

FIGS. 11A and 11B show the sensitivity and recovery time of a 25 K-ohm gold-based nanosensor, in accordance with the present embodiments, at different concentrations of hydrogen sulfide in dry air at ambient temperature and pressure. The hydrogen sulfide concentrations range from about 20 ppb$_v$ to about 1.000 ppb$_v$. In each case, the sensor sensitivity promptly reached a peak value during exposure to the test gas, and it returns to its baseline sensitivity (complete recovery) when exposure is discontinued. The sensitivity shows a substantially linear relationship to hydrogen sulfide concentration at concentrations between about 20 ppb$_v$ (the lower limit of sensitivity) and about 250 ppb$_v$ (FIG. 11B, inset), with the rate of sensitivity change decreasing at concentrations above about 250 ppb$_v$ (FIG. 11B).

Figure 12:
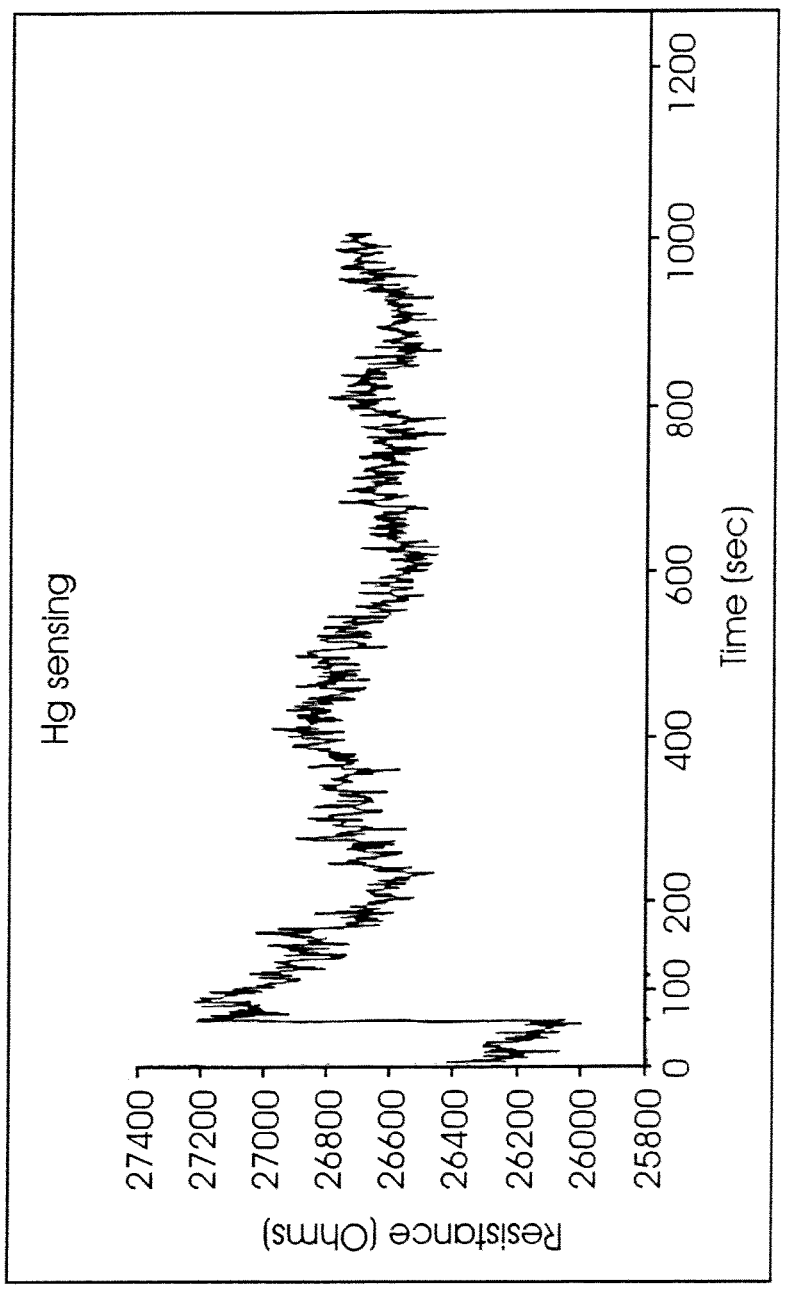
FIG. 12 is a graph showing the response (resistance-versus-time) of a gold-based gas sensor, in accordance with one aspect of the present disclosure, to mercury vapor in air at room temperature and ambient pressure.

FIG. 12 shows the response of a nominal 25 K-ohm gold-based SWNT nanosensor to mercury vapor in air at ambient pressure and room temperature. The sensor responds with a measurable increase in resistance in less than about 60 seconds, with a measurable recovery after approximately 3 minutes.

From the foregoing discussion, those of skill in the art will appreciate that electrochemical functionalization of the SWNTs using metallic nanoparticles is a simple and cost-effective technique that offers spatially-tailored functionalization. The whole process is advantageously electrochemically initiated, driven, and terminated, making the functionalization spatially localized at the electrode surface. By varying the sensor's synthesis conditions (e.g. metal electrodeposition charge, electrodeposition potential, and baseline resistance), the sensing performance may be enhanced. It is also possible to control the electrical and other physical properties of the nanosensors by controlling the plating solution concentration (metal ion concentration, supporting electrolytes, additives, complexing agents, etc.) and deposition parameters (pH, current density, applied potential, temperature, agitation, etc.). Further, the fabrication process may be performed at near room temperature without complex equipment. The resulting nanosensor is advantageously inexpensive and offers superior sensitivity and selectivity as compared to prior art gas nanosensors.

In another embodiment, the present gas sensors are based on SWNTs functionalized with polyaniline (PANI) doped with camphor-sulfonic acid (CSA). Such sensors may be used for detecting ammonia and/or nitrogen dioxide. PANI(CSA) is a typical sulfonated conducting polymer having tunable electronic properties coupled with good environmental and thermal stability. Advantageously, gas sensors comprising SWNTs functionalized with PANI(CSA) exhibit humidity independence. Thus, these sensors can be used in a wide range of environments without the need to compensate for RH, making the process of using the sensors simpler and less expensive.

A nanosensor functionalized with PANI(CSA) may be produced using methods similar to those described above with respect to metallized nanosensors and illustrated in FIG. 1 through FIG. 4D. The major difference, of course, is that a solution of PANI(CSA) nanoparticles, instead of elemental metal nanoparticles, is applied on the nanostructures 222, and the nanoparticles are functionalized in situ in steps S304 and S306 (FIG. 3), respectively.

In one exemplary embodiment, functionalized PANI (CSA)-SWNT based sensors are fabricated as follows. First, SWNTs (such as SWNT-COOH 80-90% purity, produced by Carbon Solution, Inc. of Riverside. Calif.) are dispersed (1 µg/mL) in dimethyl formamide (DMF) with ultrasonication for 1 hour. Then, the SWNTs are dispensed across microfabricated electrodes (such as the electrode network described above and illustrated in FIGS. 2A and 2B) by positioning a drop of SWNT solution using a micro-syringe or another device (steps S102 and S104, FIG. 1). The drop of SWNT solution may be, for example, 0.05 µL. After evaporation of the DMF solution, an SWNT network bridges the electrodes to form a nanostructure network. The formed and unfunctionalized nanostructure network is then annealed (step S106. FIG. 1), for example at 300° C. for 30 minutes in an inert environment (e.g., 99.999% argon), to improve the contact between the SWNTs and the electrodes.

An appropriate quantity of deoxygenated aniline and CSA in an aqueous solution is applied on the SWNT network (FIG. 3, step S304). For example, the solution may be 3 µL of deoxygenated 0.1 M aniline and 0.1 M CSA aqueous solution, although in other embodiments the concentration of either or both of the aniline and the CSA may be between 0.01 M and 1 M. Electrochemical functionalization is performed (FIG. 3, step S306) by electrodeposition, preferably with a three-electrode setup, as described above. For example, the SWNT network along with the electrodes 202 (e.g. gold electrodes) may serve as the working electrode, while a stainless steel tip and a chlorinated Ag wire serve as the counter and reference electrodes, respectively. As described above, those of skill in the art will appreciate that the electrochemical functionalization may be performed with a two-electrode setup, or by any other equivalent method. The PANI(CSA) may be deposited on the SWNTs potentiostatically (constant potential mode) at –0.8V vs. chlorinated Ag wire. Lastly, any residue may be removed from the functionalized nanostructure (FIG. 3, step S308).

Figure 13A:
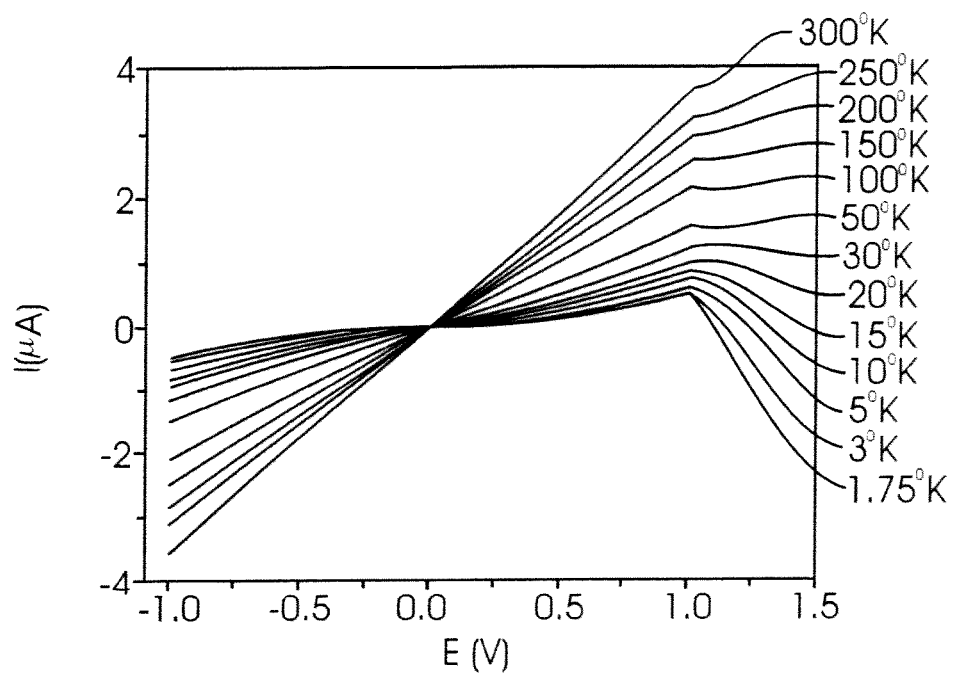
FIG. 13A is a graph illustrating the current and voltage characteristics of one embodiment of the presently-disclosed PANI(CSA)-SWNT sensors under various temperature conditions.
Figure 13B:
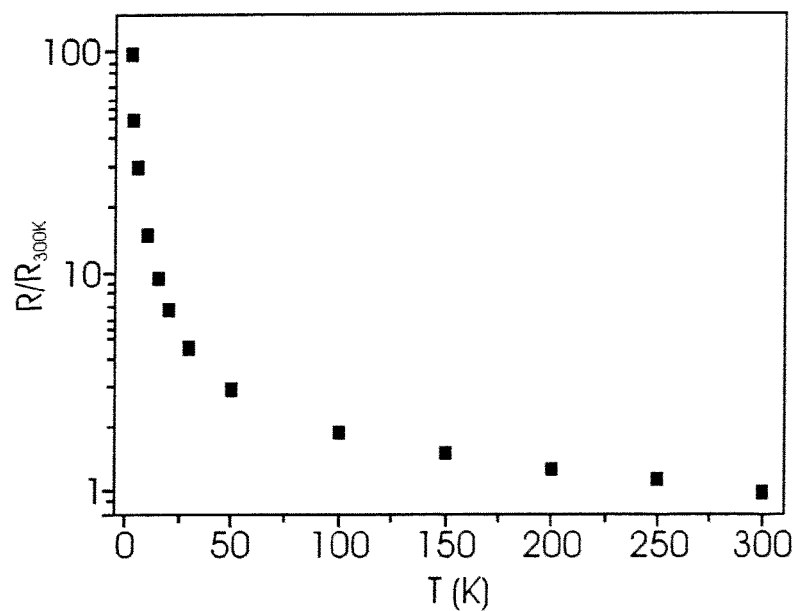
FIG. 13B is a graph illustrating a relationship of resistance to temperature for the sensor embodiment whose current and voltage characteristics are illustrated in FIG. 13A.

The coating thickness of polyaniline can advantageously be precisely adjusted by controlling the deposition time. For electronic characterization of PANI(CSA)-SWNT sensors, current (I) and voltage (V) characteristics were examined using a semiconducting parameter analyzer (HP 4155A) with the potential sweeping from –1V to 1V. The temperature-dependent electrical properties were characterized using a Physical Property Measurement System (PPMS). Thirteen measurements were taken at temperatures ranging from 1.75° K to 300° K. The I-V curves for each temperature are plotted in FIG. 13A, and the relationship of resistance to temperature is plotted in FIG. 13B. As shown in FIG. 13A, the I-V curves exhibit a slight "S" shape. The nonlinearity decreases with increasing temperature. FIG. 13B illustrates that resistance decreases rapidly with increasing temperature from about 1.75° K to about 50° K, and then decreases more gradually from about 50° K to about 300° K. These results indicate that the PANI(CSA)-SWNT network behaves as a typical semiconductor.

Several embodiments of doped polymer gas sensors were prepared for use in gas detection studies. In preparation for these studies, the gold electrodes of each sensor were wire bonded and each sensor was connected in series with a load resistor. The circuit was subjected to a fixed 1V DC potential, and the electrical resistance of the sensor was determined from continuously monitoring the voltage across the resistor, applying Ohm's law. A 3.62 cm$^3$ sealed glass chamber with gas inlet and outlet ports was positioned over the sensor chip. All experiments were conducted with known concentrations of analyte diluted in air at a total gas flow of 200 cm$^3$ per minute. The gas flow rates were regulated by mass flow controllers (Alicat Scientific Incorporated, Tucson, Ariz.). A custom Labview computer program was developed to continuously control and monitor the voltage of the circuit using Fieldpoint analog input and output modules (National Instruments, Austin, Tex.). Humidity control was generated by bubbling dry air through a bubbler. The values of relative humidity were calibrated with a thermo-hygrometer (www-.coleparmer.com) in the outlet of the flow cell. All sensing experiments were conducted at ambient conditions.

Figure 14:
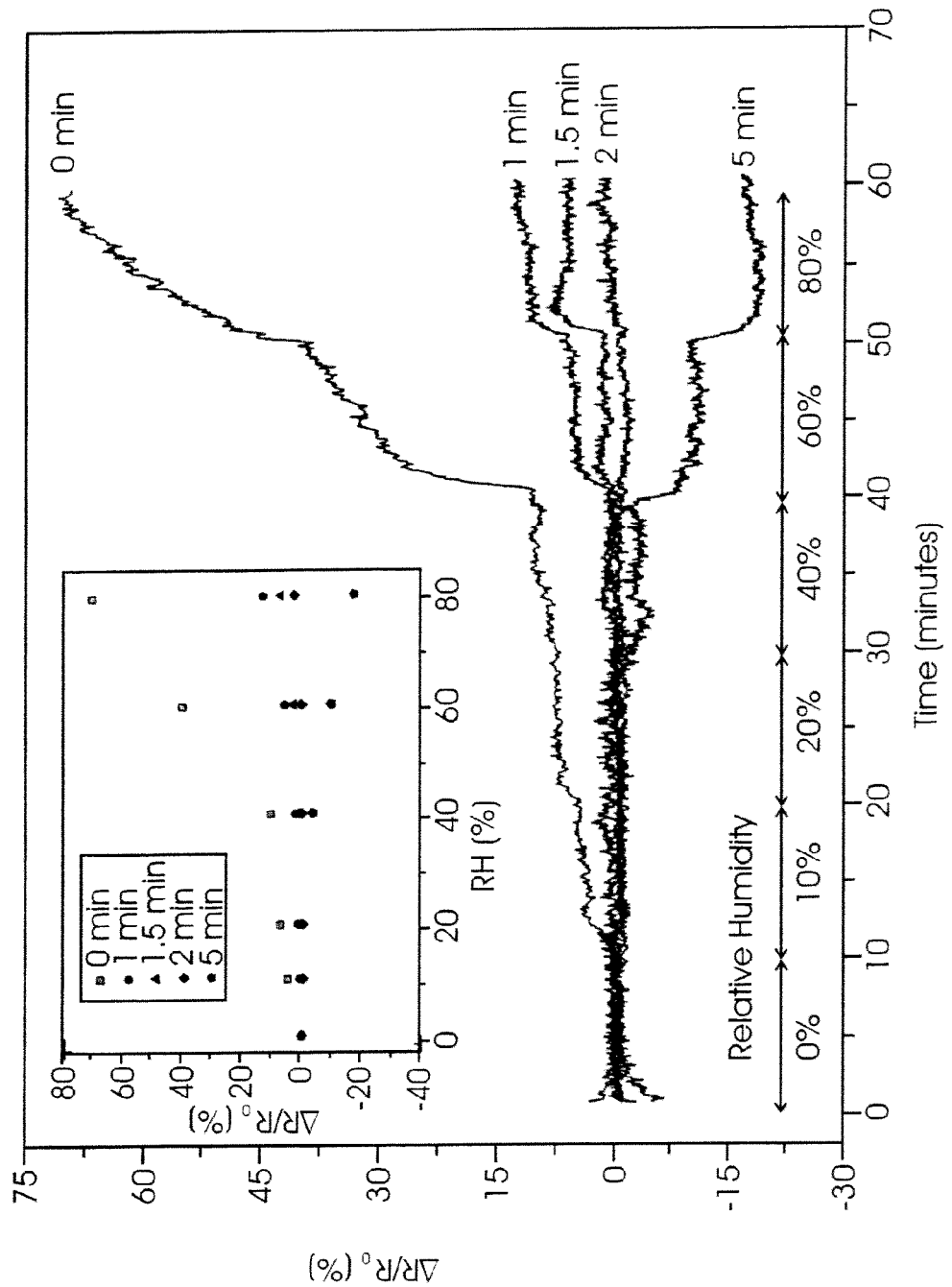
FIG. 14 is a graph illustrating the real time baseline responses to relative humidity (RH) varying from 0% to 80% in a non-condensed condition, of gas sensors in accordance with five embodiments of the presently-disclosed nanosensors.

FIG. 14 shows the real time responses of four examples of PANI(CSA)-SWNT sensors to different values of RH in the range from 0% to 80% in a non-condensed condition, as compared with an unfunctionalized SWNT sensor (0 min). The PANI(CSA)-SWNT sensors are examples with different electrodeposition times (1 min, 1.5 min, 2 min. 5 min). As discussed above, longer electrodeposition times provide thicker PANI(CSA) layers. Thus, in the above embodiments, the sensor that underwent a 1 minute electrodeposition had the thinnest PANI(CSA) layer, while the sensor that underwent a 5 minute electrodeposition had the thickest layer. The sensors were exposed to each RH value for 10 minutes to reach the steady-state resistance ($R_{eq}$). The sensitivity is defined as $$\frac{\Delta R}{R_0} \times 100,$$

which is calculated as $$\frac{R_{eq} - R_0}{R_0} \times 100,$$

where $R_0$ is the initial resistance before exposure to RH.

With reference to FIG. 14, the resistance of the unfunctionalized SWNT sensor gradually increased with RH up to about 50% RH, after which the resistance dramatically increased. For the two sensors with electrodeposition times of 1 min and 1.5 min, resistance also increased when RH rose above about 50%. However, the sensitivity to RH (11.3% and 6.4% at 80% RH) was significantly reduced compared to that of the unfunctionalized SWNT sensor (70% at 80% RH). The resistance of the PANI(CSA)-SWNT sensor with 2 min electrodeposition time is largely independent of RH change from 0% to 80%, while for the sensor with 5 min electrodeposition time, resistance decreased when exposed to RH above about 50%.

The effect of PANI(CSA) on the RH sensitivity of SWNTs results at least in part from the fact that SWNTs and PANI (CSA) have opposite electrical responses to water molecules. As discussed above, resistance in unfunctionalized SWNTs increases with increasing RH due to water molecules binding to the tubes and depleting the hole charge carriers. By contrast, the decrease in resistance of PANI(CSA) with increasing RH is thought to be from Proton Exchange-Assisted Conduction of Electrons (PEACE). Through this mechanism the conduction process of PANI(CSA) occurs through electron hopping between oxidized and reduced states. The conductivity of PANI(CSA) can be affected by different oxidation and reduction states. NMR studies have proven that proton transfer in PANI(CSA) can take place when water molecules are present: $NH_2^+ + H_2O \rightarrow NH + H_3O^+$, where water molecules act as carriers and aid in proton transport. When water molecules adsorb on PANI(CSA), the increased probability of proton exchange, along with redox reactions that change the reduced state ($NH_2^+$) to the oxidized state ($NH^+=$), results in a considerable decrease in resistivity of PANI(CSA). Since SWNT and PANI(CSA) have opposite electrical responses to water molecules, the effect of RH on SWNT sensors can be reduced by coating the SWNTs with PANI(CSA). In fact, by controlling the electrochemical functionalization of the SWNTs, sensors having resistance that is largely, if not totally, independent of RH can be produced. As discussed above, this control can be achieved by adjusting the electrodeposition time of the sensors so that the sensitivity to RH of the bare SWNTs is equal to that of the PANI(CSA) coating.

To demonstrate the performance of humidity-independent PANI(CSA)-SWNT sensors, three such sensors with different electrodeposition times (0.5 min, 2 min, 3 min) were repeatedly exposed to 10 $ppm_v$ $NH_3$ at different RH conditions. Additional sensors were exposed to $NO_2$ at different RH values. After reaching a steady state at each RH value, the sensors were purged with air for room temperature recovery. The RH was then increased, and the exposure and purging were repeated.

Figure 15:
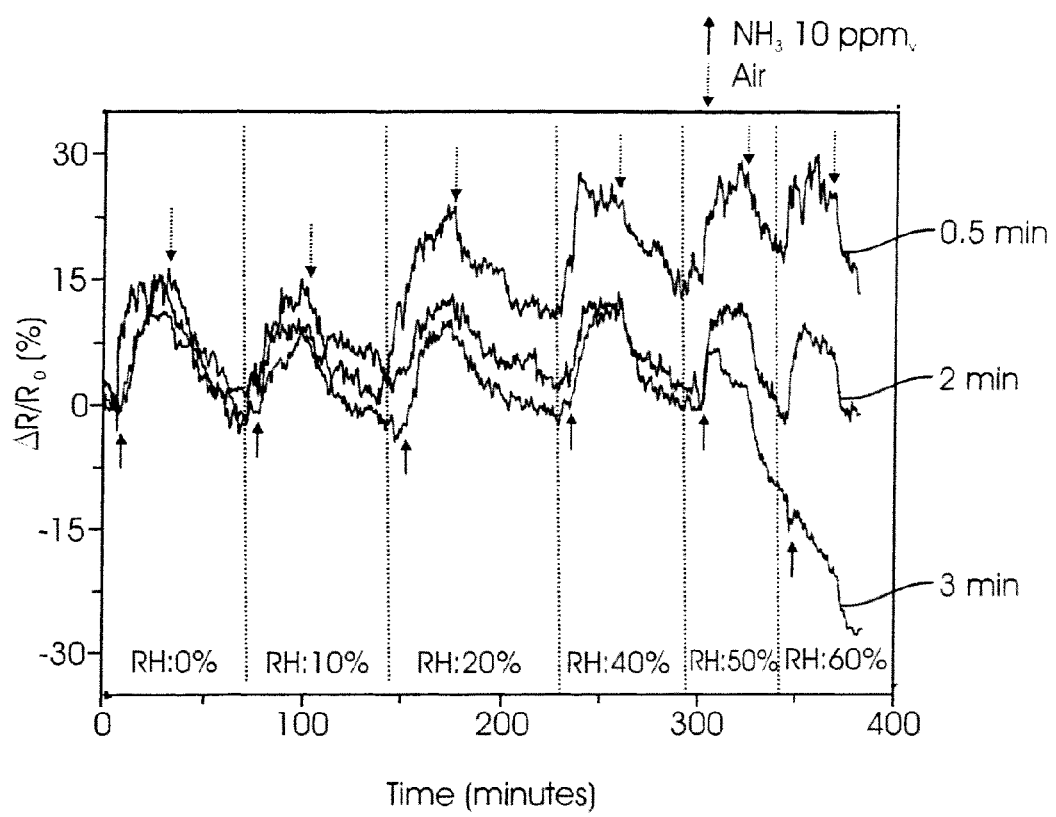
FIG. 15 is a graph illustrating the performance of PANI(CSA)-SWNT sensors, in accordance with three embodiments of the presently-disclosed nanosensors, under different RH conditions.

The results for exposure to $NH_3$ are shown in FIG. 15. Upon exposure to $NH_3$, each sensor experienced a rapid rise in resistance under all RH conditions, with the exception of the 3 min electrodeposition sensor at RH values above 50%. Upon purging with air, each sensor experienced a decrease in resistance under all RH conditions, indicating that the response to $NH_3$ is reversible in different RH conditions. As RH increased, the $R_0$ of the sensor with 0.5 minutes electrodeposition time drifted positively to around an 18% increase after operation at 60% RH. This result indicates that for an electrodeposition time of 0.5 minutes, the RH effect on the carbon of the SWNTs dominated the RH effect on the PANI(CSA) coating. By contrast, the resistance of the sensor with 3 minutes electrodeposition time dramatically decreased when RH was above 50%. This result indicates that for an electrodeposition time of 3 minutes, the RH effect on the PANI(CSA) coating dominated the RH effect on the carbon of the SWNTs. Thus, for both deposition times, RH interfered with sensor performance. By contrast, and with reference to FIG. 15, the test results for the sensor with 2 minutes of electrodeposition time demonstrate that RH had a negligible effect on the performance of that sensor. These results prove that a sensor that is largely unaffected by RH can be produced by controlling the electrodeposition time during the functionalization process.

Figure 16A:
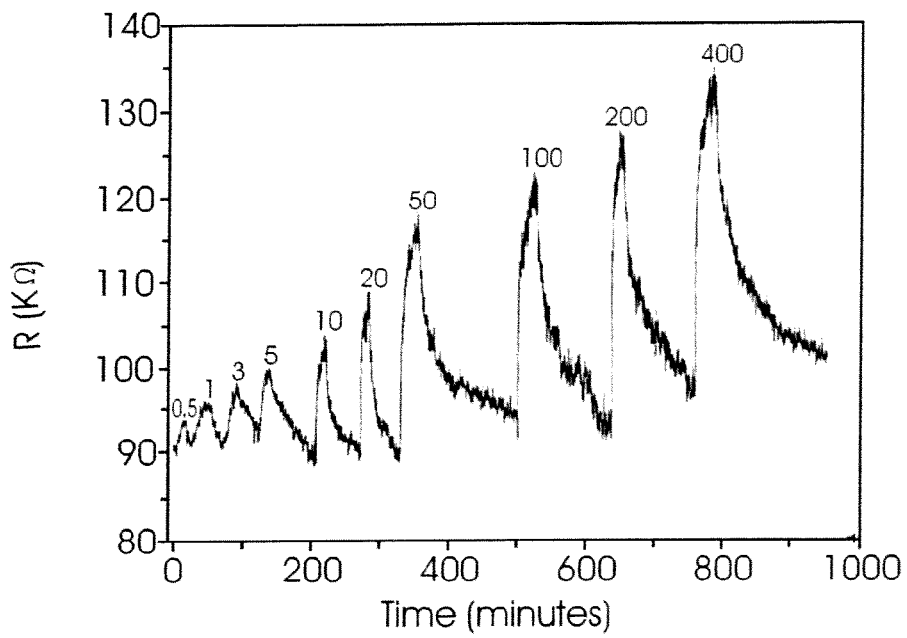
FIG. 16A is a graph illustrating the sensitivity (resistance-versus-time) of a PANI(CSA)-SWNT gas sensor to different concentrations of ammonia in dry air as a function of time.

FIG. 16A illustrates the resistance increase of a PANI (CSA)-SWNT nanosensor when exposed to increasing concentrations ranging from 0.5 $ppm_v$ to 400 $ppm_v$ of ammonia in dry air. In each case, the sensor promptly reaches a peak value during exposure to ammonia, and returns to its baseline when the ammonia feed is discontinued. The response of the PANI (CSA) functionalized SWNT nanosensor was much greater than the response of unfunctionalized SWNT nanosensors as is shown in FIG. 16B, discussed below.

Figure 16B:
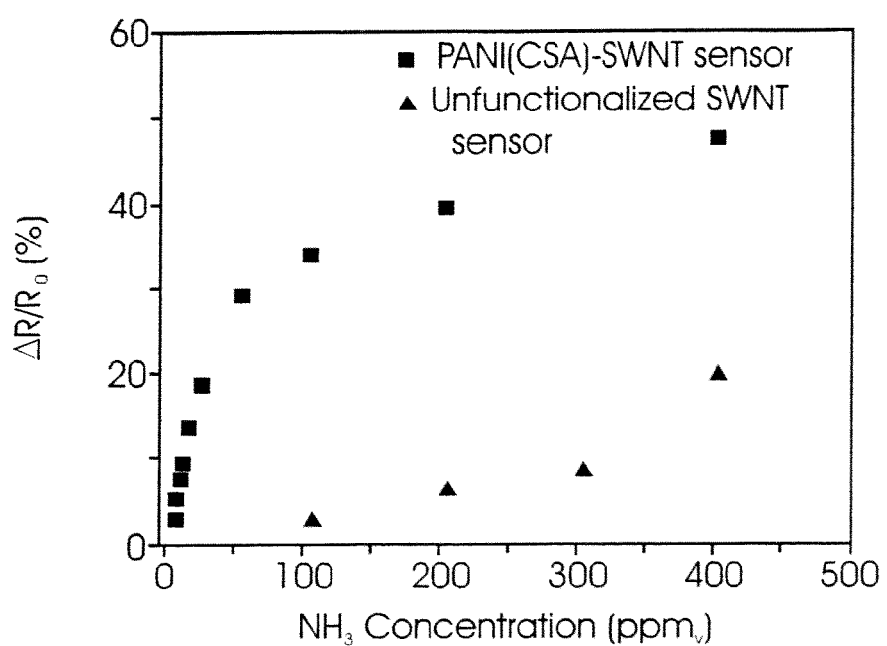
FIG. 16B is a graph comparing the response of a humidity-independent PANI(CSA)-SWNT sensor to the response of an unfunctionalized SWNT sensor to NH$_3$ from 500 ppb$_v$ to 400 ppm$_v$ at 0% RH.

FIG. 16B compares the responses of a humidity-independent PAN (CSA)-SWNT and an unfunctionalized SWNT sensor to $NH_3$ from 500 $ppb_v$ to 400 $ppm_v$ at 0% RH. The sensitivity of the PANI(CSA)-SWNT is much higher than that of the unfunctionalized SWNT sensor. The higher sensitivity of the PANI(CSA)-SWNTs results at least in part from the great affinity of $NH_3$ to PANI(CSA) because of the coordinating roles of the nitrogen atoms of both compounds, and the deprotonation-protonation process brought by adsorbed-desorbed According to the results, the PANI(CSA)-SWNT sensor shows superior sensitivity, very low detection limit, and faster response time compared to the bare SWNT sensor.

Those of skill in the art will appreciate that the above disclosure demonstrates facile electrochemical methods to fabricate humidity-independent PANI(CSA) functionalized SWNT gas sensors that have demonstrated outstanding sensing properties. Because of the opposite electrical response to RH of SWNTs and PANI(CSA), it is possible to eliminate RH interference on PANI(CSA)-SWNT sensor performance by controlling the amount of PANI(CSA) electrodepositing onto SWNTs. The electrochemical functionalization method allows precisely controlled PANI(CSA) thickness coated onto SWNTs by simply adjusting electrodeposition time, in contrast to the chemical functionalization method, in which it is difficult to control the amount of polymer coating. Depending on the particular application and the performance criteria to be met, the PANI (CSA) nanoparticles may be deposited to a thickness in the range of about 5-500 nm for use in gas sensors.

Other polyaniline dopants have been successfully tested in gas sensing experiments. For example, SWNTs have been functionalized with polyaniline doped with chloride ($Cl^-$), perchlorate ($ClO_4^-$), acrylic acid ($C_3H_4O_2$), tetraethylammonium perfluorooctane sulfonate (TEAPFOS) and para-toluene sulfonic acid ($CH_3C_6H_4SO_3H$). Chloride embodiments (which are not RH independent) have been successfully tested for sensing ammonia ($NH_3$), nitrogen dioxide ($NO_2$) and water vapor. Embodiments of perchlorate, acrylic acid, tetraethylammonium perfluorooctane sulfonate and para-toluene sulfonic acid (which are likewise not RH independent) have been successfully tested for sensing ammonia and water vapor.

Electrochemical functionalization is a simple and cost-effective technique that offers spatially-tailored functionalization. The fabrication methods described above allow for precise control over a sensor's characteristics and make it possible to create arrays of individually addressable sensors, each functionalized with a different substance. Such arrays are capable of displaying different sensor characteristics, simultaneously analyzing a range of different species, and may include redundancies to reduce false positives and negatives. In certain embodiments, PANI(CSA) can be electrodeposited onto SWNTs, while the thickness and morphology of the coated PANI(CSA) layer can advantageously be precisely controlled by adjusting deposition time. With different thickness of PANI(CSA) deposited, the response of the sensors to RH can be tuned until it is negligible.

In another embodiment, the presently-disclosed gas sensors are based on SWNTs electrochemically functionalized with a metal oxide. In an exemplary embodiment, SWNTs are functionalized with tin oxide. Metal oxide surfaces have electrically and chemically active oxygen vacancies. Certain gas molecules, on interacting with the surface of metal oxides, react with these oxygen vacancies, altering their conductivity. Gas sensors use this property to detect variety of analyte gases, such as methane, ammonia and NOx. In an exemplary embodiment. SWNTs functionalized with tin oxide are provided.

In one exemplary embodiment, electrochemically functionalized metal oxide based sensors are fabricated as follows. First, SWNTs (such as SWNT-COOH 80-90% purity, produced by Carbon Solution, Inc. of Riverside, Calif.) are dispersed (1 μg/mL) in dimethyl formamide (DMF) with ultrasonication for 1 hour. Then, the SWNTs are dispensed across microfabricated electrodes (such as the electrode network described above and illustrated in FIGS. 2A and 2B) by positioning a drop of SWNT solution using a micro-syringe or another device (steps S102 and S104. FIG. 1). The drop of SWNT solution may be, for example, 0.05 μL. After evaporation of the DMF solution, an SWNT network bridges the electrodes to form sensors. The formed and unfunctionalized sensors are then annealed (step S106. FIG. 1), for example at 300° C. for 30 minutes in an inert environment (e.g., 99.999% argon), to improve the contact between the SWNTs and the electrodes.

Electrochemical functionalization is then performed with a three-electrode setup (steps S304 and S306, FIG. 3). For example, the SWNT network along with the electrodes 202 (e.g. gold electrodes) may serve as the working electrode, while a platinum wire and chlorinated Ag wire serve as the counter and reference electrodes, respectively. As described above, those of skill in the art will appreciate that the electrochemical functionalization may be performed with a two-electrode setup, or by any other equivalent method. For electrodeposition of metal oxides on SWNTs, presence of OH$^-$ ions or O$^-$ ions near the electrode surface is required. An oxidizing agent, such as hydrogen peroxide, blown oxygen, or nitric acid, is used in the solution. In an exemplary embodiment, nitric acid is used in the electroplating solution. For nitric acid the reaction at the cathode is:

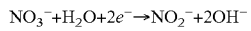

$$NO_3^- + H_2O + 2e^- \rightarrow NO_2^- + 2OH^-$$

The presence of OH$^-$ ions near the vicinity of electrode surface increases the pH which drives the local precipitation of the metal ions.

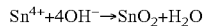

$$Sn^{4+} + 4OH^- \rightarrow SnO_2 + H_2O$$

Direct electrodeposition of tin oxide on SWNTs is performed using an electrochemical solution of 20 mM SnCl$_2$, 75 mM HNO$_3$ and 100 mM NaNO$_3$. The pH of the solution is maintained at 1.3. After deposition, the sensors are rinsed with water and annealed at 400° C. under argon atmosphere for 4 hours.

Figure 17:
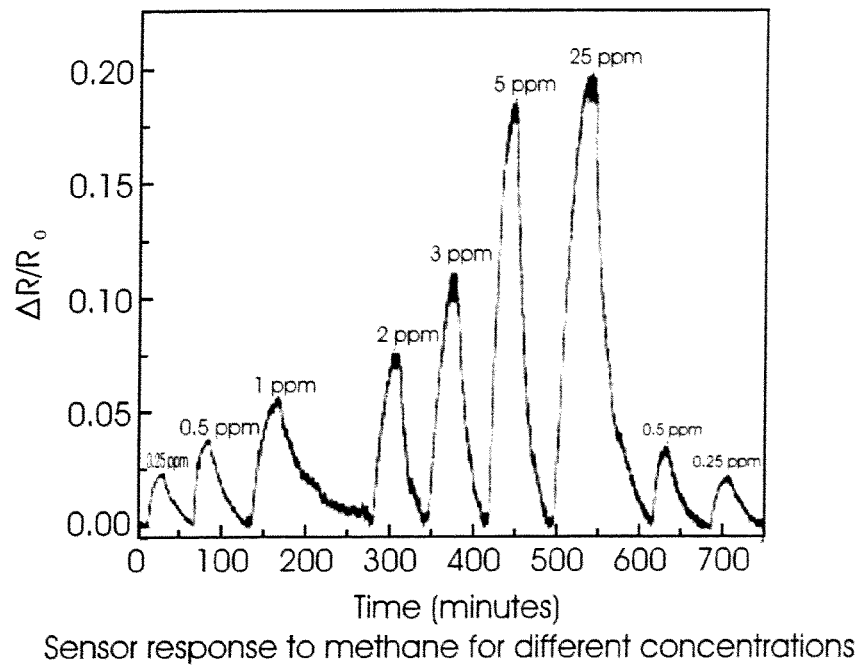
FIG. 17 is a graph illustrating the sensitivity of a tin oxide gas nanosensor to methane, at several different methane concentrations.
Figure 18:
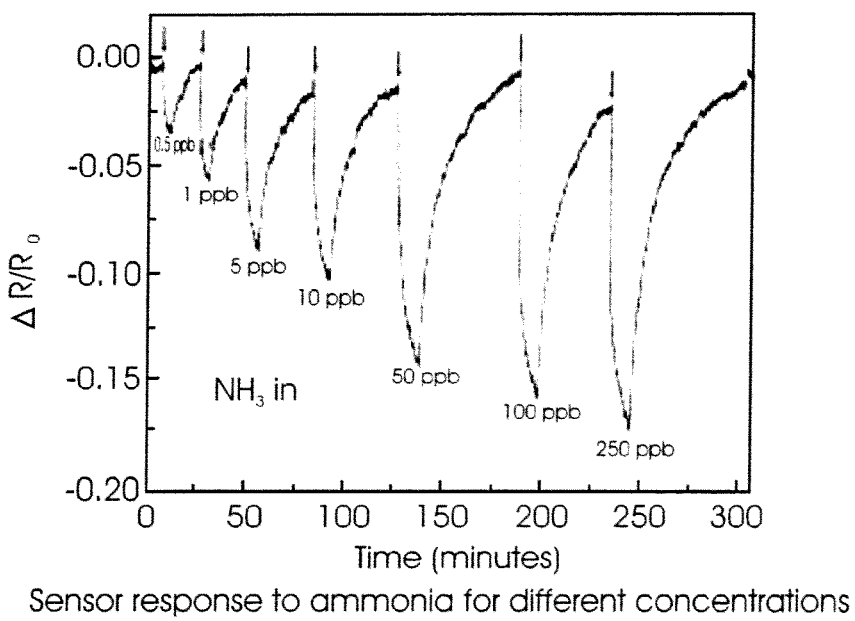
FIG. 18 is a graph illustrating the sensitivity of a tin oxide nanosensor to ammonia, at several different ammonia concentrations.

FIG. 17 illustrates the relative resistance changes (sensitivity) of a tin oxide (SnO$_2$) nanosensor to various short term exposures to methane at increasing concentrations ranging from 0.25 to 25 ppm$_v$ and the return to the baseline signal. FIG. 18 shows response of a tin oxide sensor to varying exposures to ammonia gas in air in increasing concentrations ranging from 0.5 ppb$_v$ to 250 ppb$_v$. There is a sharp decrease of the resistance is observed upon exposure to ammonia. Tin oxide sensors may also be used to detect NO$_2$ at concentrations below 50 ppm$_v$, and H$_2$S concentrations greater than at least 10 ppm$_v$.

The present disclosure provides a description of the best modes currently contemplated for making and using the nanomaterial-based gas sensors disclosed herein, in such full, clear, concise, and exact terms as to enable any person skilled in the art to which it pertains to make and use these sensors. The sensors and methods disclosed herein are, however, susceptible to modifications and alternate constructions from those discussed above. By way of example, a gas sensor chip may be constructed according to this disclosure that includes several nanostructure networks functionalized with different types of nanoparticles so as to be sensitive to two or more different gases. Consequently, this disclosure encompasses not only the particular embodiments explicitly disclosed herein, but also any equivalents that may reasonably suggest themselves to those skilled in the pertinent arts. Thus, this disclosure encompasses all modifications and alternate constructions coming within the spirit and scope of this disclosure, as generally expressed by the following claims.

What is claimed is:

1. A method of manufacturing a device for sensing a specific gas in a gaseous environment, the method comprising the steps of:
   (a) forming an array of conductive electrodes on a substrate;
   (b) forming a nanostructure network having a specified electrical parameter by (i) placing on the array a nanomaterial suspension comprising a nanomaterial dispersed in a solvent, wherein the nanomaterial is selected from the group consisting of at least one of single-walled carbon nanotubes, multi-walled carbon nanotubes, silicon nanowires, zinc oxide nanostructures, tin oxide nanowires, indium oxide nanowires, carbon boride nanotubes, carbon nitride nanotubes, and general B$_x$C$_y$N$_z$ nanotube structures; and (ii) drying the nanomaterial suspension to leave a nanomaterial structure on the electrodes in the array;
   (c) annealing the nanostructure network; and
   (d) electrodepositing nanoparticles on the nanostructure network, wherein the nanoparticles are made of a material that, when applied to the nanostructure network, alters the selected electrical parameter in the presence of the specific gas, wherein the material of the nanoparticles is selected from the group consisting of metal nanoparticles, doped polyaniline nanoparticles, and metal oxide nanoparticles.

2. The method of claim 1, wherein the metal nanoparticles are selected from the group consisting of palladium nanoparticles and gold nanoparticles.

3. The method of claim 1, wherein the nanoparticles are metal nanoparticles, and the step of electrodepositing the nanoparticles on the nanostructure network includes electrolytically depositing the metal nanoparticles on the nanostructure network.

4. The method of claim 1, wherein the nanoparticles are doped polyaniline nanoparticles, and the step of electrodepositing the nanoparticles on the nanostructure network includes electrolytically depositing the doped polyaniline nanoparticles on the network.

5. The method of claim 1, wherein the nanoparticles are metal oxide nanoparticles, and the step of electrodepositing the nanoparticles on the nanostructure network includes electrolytically depositing the metal oxide nanoparticles on the nanostructure network.

6. The method of claim 1, wherein the step of forming the nanostructure network comprises the step of forming a pattern of conductive electrodes on a substrate.

7. The method of claim 4, wherein the doped polyaniline particles are made from polyaniline and a dopant selected from the group consisting of camphor-sulfonic acid (CSA), perchlorate ($ClO_4^-$), acrylic acid ($C_3H_4O_2$), tetraethylammonium perfluorooctane sulfonate (TEAPFOS), and para-toluene sulfonic acid ($CH_3C_6H_4SO_3H$).

8. The method of claim 7, wherein the nanoparticles are made of camphor-sulfonic acid (CSA)-doped polyaniline, and wherein the step of electrodepositing the nanoparticles includes the steps of applying an aqueous solution of deoxygenated 0.01 M to 1 M aniline and 0.01 M to 1 M CSA on the nanostructure network, and applying electrolysis to the solution to electrolytically deposit CSA-doped polyaniline nanoparticles onto the nanostructure network.

9. The method of claim 1, wherein the substrate is made of a semiconductor material.

10. The method of claim 9, wherein the semiconductor material is silicon.

11. The method of claim 10, wherein the substrate includes a passivation layer.

12. The method of claim 11, wherein the passivation layer is made of silicon dioxide.

13. The method of claim 1, wherein the nanomaterial comprises single-walled carbon nanotubes (SWNTs).

14. The method of claim 13, wherein the SWNTs are dispersed in the solvent in a concentration in the range of 0.01 μg/mL to 1.0 μg/mL.

15. The method of claim 2, wherein the metal nanoparticles are gold nanoparticles.

* * * * *